US009492441B2

(12) United States Patent
DiSanto

(10) Patent No.: US 9,492,441 B2
(45) Date of Patent: Nov. 15, 2016

(54) DRUG TREATMENT OF OVERACTIVE BLADDER

(76) Inventor: Michael E. DiSanto, Burlington, NJ (US)

(*) Notice: Subject to any disclaimer, the term of this patent is extended or adjusted under 35 U.S.C. 154(b) by 0 days.

(21) Appl. No.: 14/118,448

(22) PCT Filed: May 17, 2012

(86) PCT No.: PCT/US2012/038393
§ 371 (c)(1),
(2), (4) Date: Jan. 27, 2014

(87) PCT Pub. No.: WO2012/158942
PCT Pub. Date: Nov. 22, 2012

(65) Prior Publication Data
US 2014/0200238 A1 Jul. 17, 2014

Related U.S. Application Data

(60) Provisional application No. 61/487,329, filed on May 18, 2011.

(51) Int. Cl.
A61K 45/06 (2006.01)
A61K 31/4745 (2006.01)
H04B 1/16 (2006.01)
H03L 1/02 (2006.01)

(52) U.S. Cl.
CPC ........... *A61K 31/4745* (2013.01); *A61K 45/06* (2013.01); *H03L 1/026* (2013.01); *H04B 1/16* (2013.01)

(58) Field of Classification Search
CPC .. H03L 1/026; A61K 45/06; A61K 31/4745; H04B 1/16
See application file for complete search history.

(56) References Cited

U.S. PATENT DOCUMENTS

2011/0105554 A1    5/2011   Manstein et al.

OTHER PUBLICATIONS

Zhang et al., 2010, BJUI, pp. 310-317.*
Lucas-Lopez, 2008, caplus an 2008:667946.*
Lucas-Lopez#2, 2005, caplus an2005:424459.*
Xinhua Zhang et al.; Blebbistain, a Myosin II Inhibiotr, as a Novel Strategy to Regulate Detrusor Contractility in a Rat Model of Partial Bladder Outlet Obstruction; Public Library of Science, Oct. 2011, vol. 6, Issue 10.
Xinhua Zhang et al.; Update on Corpus Cavemosum Smooth Muscle Contractile Pathways in Erectile Function: A Role for Testosterone?; 2011 International Society for Sexual Medicine; Journal of Sexual Medicine.
Xinhua Zhang et al.; In vitro and in vivo Relaxation of Urinary Bladder Smooth Muscle by the Selective Myosin II Inhibitor, Blebbistatin; (Abstract) World Chinese Urological Society Annual Meeting at 2010 Annual Meeting of the American Urological Association, San Francisco, May 2010.
Xinhua Zhang et al.; In Vitro and in Vivo Relaxation of Urinary Bladder Smooth Muscle by the Selective Myosin II Inhibitor, Blebbistatin; BJUI, BJU International, 2010 0.
Katherine S. Sandhu et al.; Regional Heterogeneity in Expression of the Sphingosine-1-Phosphate Pathway in the Female Rat Lower Urinary Tract; American Journal of Obstetrics & Gynecology, May 2009.
Xinhua Zhang et al.; In Vitro and in Vivo Relaxation of Corpus Cavemosum Smooth Muscle by the Selective Myosin II Inhibitor, Blebbistatin; International Society for Sexual Medicine; Journal of Sexual Medicine, 2009, 6, pp. 2661-2671.
Cristina Lucas-Lopez et al.; the Small Molecule Tool (S)-(-)-Blebbistatin: Novel Insights of Relevance to Myosin Inhibitor Design; The Royal Society of Chemistry, Organic & Biomolecular Chemistry, 2008, 6, pp. 2076-2084.
Thomas J. Eddinger et al.; Potent Inhibition of Arterial Smooth Muscle Tonic Contractions by the Selective Myosin II Inhibitor, Blebbistatin; The Journal of Pharmacology and Experimental Therapeutics, 2007, vol. 230, No. 2, pp. 865-870.
Karl-Erik Andersson et al.; Phosphodiesterases (PDEs) and PDE Inhibitors for Treatment of Luts; Neurology and Urodynamics, 2007, 26, pp. 928-933.
Xinhua Zhang et al.; Smooth Muscle Myosin Expression, Isoform Composition, and Functional Activities in Rat Corpus Cavemosum Altered by the Streptozotocin-Induced Type 1 Diabetes; American Journal of Physiological Endocrinol Metabolism, 392, E32-E42, 2012.
Sylvia O. Suadicani et al.; Effects of Ageing and Streptozotocin-Induced Diabetes on Connexin43 and P2 Purinoceptor Expression in the Rat Corpora Cavernosa and Urinary Bladder; BJUI, BJU International, 2009, 103, 1686-1693.
Arnold Melman et al.; Longitudinal Studies of Time-Dependent Changes in Both Bladder and Erectile Function After Streptozotocin-Induced Diabetes in Fischer 344 Male Rats; BJUI, BJU International, 2009, 104, 1292-1300.

(Continued)

*Primary Examiner* — Sun Jae Yoo
(74) *Attorney, Agent, or Firm* — Howard M. Cohn; Daniel M. Cohn

(57) ABSTRACT

Provided are methods of treating an overactive bladder in a patient which include: administering a Myosin II ATPase inhibitor compound; or administering an X group and Y group substituted (3a-hydroxy-1-phenyl-1,2,3,3a-tetrahydro-4H-pyrrolo[2,3b]quinolin-4-one) compound of Formula 1 or administering an X group and Y group substituted (3a-hydroxy-1-phenyl-1,2,3,3a-tetrahydro-4H-pyrrolo[2,3b]quinolin-4-one) compound of Formula II; or administering pharmaceutically-acceptable salts, racemic mixtures, enantiomers, or prodrugs of said compounds, useful in their active form as inhibitors of Myosin H ATPase related to over-active bladder. Optionally the compounds are administered intervesicularly into the bladder. Also provided are pharmaceutical compositions comprising said compounds useful in their active form, as methods of treating a patient suffering from an over-active bladder related to inhibition of Myosin II ATPase. These pharmaceutical compositions also may contain one or more other compounds useful in their active form, as methods of treating a patient suffering from an over-active bladder.

12 Claims, 7 Drawing Sheets

(56) References Cited

OTHER PUBLICATIONS

Karl-Erik Andersson et al.; Pharmacological Treatment of Overactive Bladder: Report from the International Consultation on Incontinence; Current Opinion in Urology, 2009, 19:380-394.

Antonella Giannantoni et al.; New Frontiers in Intravesical Therapies and Drug Delivery; European Association of Urology, European Urology 50, 2006; pp. 1183-1193.

Pradeep Tyagi et al.; Local Drug Delivery to Bladder Using Technology Innovations; Urologic Clinics of North America, 33, 2006; pp. 519-530.

Mari Ekman et al.; Decreased Phosphatase Activity, Increased Ca2+ Sensitivity, and Myosin Light Chain Phosphorylation in Urinary Bladder Smooth Muscle of Newborn Mice; Journal of General Physiology, vol. 125, Feb. 2005, pp. 187-196.

Elfaridah P. Frazier et al.; Does Cyclic AMP Mediate Rat Urinary Bladder Relaxation by Isoproterenol?; The Journal of Pharmacology and Experimental Therapeutics, 2005, vol. 313, No. 1, pp. 260-267.

Cristina Lucas-Lopez et al.; Absolute Stereochemical Assignment and Fluorescence Tuning of the Small Molecule Tool (-)-Blebbistatin; European Journal of Organic Chemistry, 2005, pp. 1736-1740.

Stephen Patterson et al.; Selective Chemical Intervention in Biological Systems: the Small Molecule Tool, S-(-)-Blebbistatin; Beilstein-Institut, The Chemical Theatre of Biological Systems, May 24-28, 2004; Bozen, Italy.

Mihaly Kovacs et al; Mechanism of Blebbistatin Inhibition of Myosin II; The Journal of Biological Chemistry, vol. 279, No. 34, Aug. 20, 2004; pp. 35557-35563.

John Limouze et al.; Specificity of Blebbistatin, an Inhibitor of Myosin II; Journal of Muscle Research and Cell Motility, 25, pp. 337-341, 2004.

Stephen Patterson et al; Rapid Access to a Pentacyclic Library Core Structure: A Microwave Assisted Approach; QSAR & Combined Sciences; 2004, 23, pp. 883-890.

Aaron F. Straight et al.; Dissecting Temporal and Spatial Control of Cytokinesis with a Myosin II Inhibitor, Science, vol. 299, Mar. 14, 2003; pp. 1743-1747.

Con J. Kelleher et al.; Health-Related Quality of Life of Patients Receiving Extended-Release Tolterodine for Overactive Bladder; The American Journal of Managed Care, Dec. 2002; vol. 8, No. 19SUP, pp. S608-S615.

Matthew O. Fraser et al.; The Future of Bladder Control-Intravesical Drug Delivery, a Pinch of Pepper, and Gene Therapy; Reviews in Urology, vol. 4, No. 1, 2002.

John P. Lavelle et al.; Urothelial Pathophysiological Changes in Feline Interstitial Cystitis; a Human Model; American Journal of Physiological Renal Physiology, 278, pp. F540-F553, 2000.

Michiko Yamamoto et al.; Parathyroid Hormone-Related Protein in the Rat Urinary Bladder: a Smooth Muscle Relaxant Produced Locally in Response to Mechanical Stretch; Procedures National Academy of Science, USA, Physiology; vol. 89, pp. 5326-5330; Jun. 1992.

A. Malmgren et al.; Bladder Function in Rats with Short- and Long-term Diabetes; Effects of Age and Muscarinic Blockade; Journal of Urology, 142(6) pp. 1608-1614; Dec. 1989.

Rowena G. Chua et al.; Testosterone Regulates Erectile Function and Vcsa1 Expression in the Corpora of Rats; Molecular and Cellular Endocrinology 303, pp. 67-73; 2009.

\* cited by examiner

DRUG TREATMENT OF OVERACTIVE BLADDER

CROSS-REFERENCE TO RELATED APPLICATION

This application claims the benefit to priority of U.S. Provisional Application with Ser. No. 61/487,329 filed May 18, 2011.

GOVERNMENT FUNDING

The U.S. Government has a paid-up license in this invention and the right in limited circumstances to require the patent owner to license others on reasonable terms as provided for by terms of research grant contract number 5RO1DK077116 awarded by the National Institutes of Health (NIH).

FIELD OF THE INVENTION

The present invention relates to methods of treatment of over active bladder using Myosin ATPase inhibitor compounds, including substituted 3a-hydroxy-1-phenyl-1,2,3,3a-tetrahydro-4H-pyrrolo[2,3b]quinolin-4-one compounds which in their active form can inhibit Myosin II ATPase.

BACKGROUND OF THE INVENTION

Lower urinary tract (LUT) dysfunction can include an overactive bladder (OAB). The bladder's smooth muscle is referred to as the detrusor muscle. The main symptoms of an overactive bladder are an increased day-time and night-time frequency of urination, an increased frequency of the urge to urinate and a reduced ability to control urination. OAB is increasing in the ageing population and there are few highly-effective or tolerable treatments (Kelleher C J, Kreder K J, Pleil A M, Burgess S M, Reese P R, "Health-related quality of life of patients receiving extended-release tolterodine for overactive bladder" Am J Manag. Care 2002; 8: S608-15).

A cause of OAB may be a frequent or an excessive release of acetylcholine from cholinergic nerves innervating or terminating near the bladder smooth muscle. A common pharmaceutical therapy for OAB is administration of an anti-muscarinic drug to block the excessive acetylcholine from binding to acetylcholine receptors. Unfortunately, such anti-muscarinic therapy has only a 65-75% efficacy in treating major symptoms of overactive bladder (OAB) in a patient, and its use is limited due to drug side effects such as blurred vision, dry mouth and constipation. (Zhang, X, Kuppam, D S R, Melman, A, DiSanto, M E. "In vitro and In vivo relaxation of urinary bladder smooth muscle by the selective Myosin II inhibitor, blebbistatin" BJU Internat. e-publication 2010, journal publication, 2011; Volume 107, Issue 2, pages 310-317). About 75% of the OAB patients discontinue taking an anti-muscarinic drug to treat OAB because the patient finds such side effects intolerable.

Various types of drugs for a treatment of OAB include using α-adrenergic antagonists, β-adrenoceptor agonists, membrane channel activity modulators, phosphodiesterase inhibitors, and prostaglandin-synthesis inhibitors (Andersson K E, Chapple C R, Cardozo L et al. "Pharmacological treatment of overactive bladder: report from the International Consultation on Incontinence" Curr Opin Urol 2009; 19: 380-94). Some pharmaceutical drug therapies for OAB modify the myogenic pathway of the bladder's smooth muscle (detrusor muscle) (Yoshimura N, Kaiho Y, Miyazato M et al. "Therapeutic receptor targets for lower urinary tract dysfunction." Naunyn Schmiedebergs Arch Pharmacol 2008; 377: 437-48). Myogenic pathways are believed to be an important trigger for detrusor muscle contraction and relaxation cycling. In smooth muscle there are changes in cell membrane tension during the muscle contraction and relaxation cycle. The stretch declines during muscle contraction and increases during muscle relaxation. Increased membrane tension opens membrane ion channels whose conductance depolarizes the cell transmembrane potential. The change in transmembrane potential increases cytoplasmic calcium ion levels and other biochemical processes which stimulate muscle contraction. Contraction relieves membrane tension and the processes reverse during muscle relaxation when membrane tension has again increased due to muscle lengthening. Different smooth muscle organs vary in degree, frequency and time profile of their contractions. The response of different smooth muscles to drugs is unpredictable. It is appreciated that there is serial and parallel biochemical signal processing and often with positive and negative feedback controls. Also, there can be changes in genetic expression of smooth muscle during development and aging. Endocrine and exocrine processes also modulate smooth muscle function. It is not obvious how to develop an effective and tolerable pharmaceutical treatment for an overactive bladder smooth muscle.

SUMMARY OF THE INVENTION

According to the invention there is disclosed a method of treating an overactive bladder in a patient, which method comprises: administering to said patient an effective amount of a Myosin II ATPase inhibitor compound, or a pharmaceutically-acceptable salt, a racemic mixture, an enantiomer thereof; optionally administering a drug selected from the group consisting of a PDE5 inhibitor drug and an antimuscarininc drug, and optionally administering to the bladder directly or intervesiculary an effective amount the a Myosin II ATPase inhibitor compound, a pharmaceutically-acceptable salt, a racemic mixture, an enantiomer, or a prodrug thereof, to the overactive bladder of the patient.

Further according to the invention, the invention also provides pharmaceutical compositions comprising an effective amount of a Myosin II ATPase inhibitor compound, useful in its active form, as a method of treating an overactive bladder in a patient.

Still further according to the invention, there is also disclosed a method of treating an overactive bladder in a patient, which method comprises administering to said patient an effective amount of a Myosin II ATPase inhibitor compound of Formula (1) or a pharmaceutically-acceptable salt, a racemic mixture, an enantiomer, or a prodrug thereof,

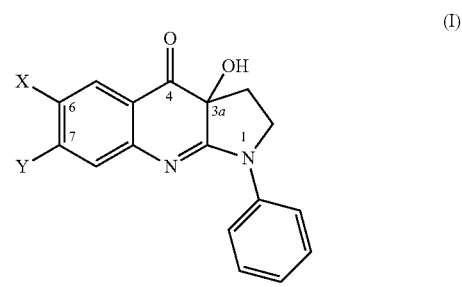

(I)

wherein:

X is selected from the group consisting of hydrogen, methyl, hydroxy, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[(C_{1-6})$alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$, $(C_{1-6})$alkylaminoketo, acetoxy, carb$(C_{1-6})$alkoxy, $(C_{1-6})$alkyl-C(=O)—O—$(C_{1-6})$alkyl, $(C_{1-6})$alkyl-O—C(=O)—$(C_{1-6})$alkyl, acetamido, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenylalanyl, tyrosinyl, trptophanyl, threonyl, cystinyl, asparginyl, glutamyl, lysinyl, histidinyl, arginyl, aspartyl, and glutamyl, optionally substituted at a carbon atom with a substituent W, the substituent W selected from the group consisting of methyl, hydroxy, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[(C_{1-6})$alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$, $(C_{1-6})$alkylaminoketo, acetoxy, carb$(C_{1-6})$alkoxy, $(C_{1-6})$alkyl-C(=O)—O—$(C_{1-6})$alkyl, $(C_{1-6})$alkyl-O—C(=O)—$(C_{1-6})$alkyl, acetamido, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenyklalanyl, tyrosinyl, trytophanyl, threoninyl, cystinyl, asparginyl, glutamyl, lysinyl, histidinyl, arginyl, aspartyl, and glutamyl, and optionally substituted at a primary nitrogen atom or at a secondary nitrogen atom with a substituent Q, the substituent Q selected from the group consisting of methyl, $(C_{1-6})$alkyl, cyclopropyl, $(C_{2-6})$alkenyl, $(C_{2-6})$alkynl, $(C_{1-6})$haloalkyl, $(C_{3-7})$cycloalkyl, $(C_{4-7})$cycloalkenyl, phenyl, benzyl, napthyl, $(C_{4-8})$heterocyclic, $(C_{4-10})$aryl, $(C_{4-10})$haloaryl, and $(C_{4-8})$heteroaryl; wherein Y is selected from the group consisting of hydrogen, methyl, hydroxy, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[(C_{1-6})$alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$, carbamyl, $(C_{1-6})$alkylaminoketo, acetoxy, carb$(C_{1-6})$alkoxy, $(C_{1-6})$alkyl-C(=O)—O—$(C_{1-6})$alkyl, $(C_{1-6})$alkyl-O—C(=O)—$(C_{1-6})$alkyl, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenyklalanyl, tyrosinyl, trytophanyl, threoninyl, cystinyl, asparginyl, glutamyl, lysinyl, histidinyl, arginyl, aspartyl, and glutamyl, optionally substituted at a carbon atom with a substituent Z, the substituent Z selected from the group consisting of methyl, hydroxy, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio $(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[(C_{1-6})$alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$, carbamyl, $(C_{1-6})$alkylaminoketo, acetoxy, carb$(C_{1-6})$alkoxy, $(C_{1-6})$alkyl-C(=O)—O—$(C_{1-6})$alkyl, $(C_{1-6})$alkyl-O—C(=O)—$(C_{1-6})$alkyl, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenylalanyl, tyrosinyl, tryptophanyl, threonyl, cystinyl, asparginyl, glutamyl, lysinyl, histidinyl, arginyl, aspartyl, and glutamyl, and optionally substituted at a primary nitrogen atom or at a secondary nitrogen atom with a substituent T, the substituent T selected from the group consisting of methyl, $(C_{1-6})$alkyl, cyclopropyl, $(C_{2-6})$alkenyl, $(C_{2-6})$alkynl, $(C_{1-6})$haloalkyl, $(C_{3-7})$cycloalkyl, $(C_{4-7})$cycloalkenyl, phenyl, benzyl, $(C_{4-10})$aryl, napthyl, $(C_{4-10})$haloaryl, $(C_{4-8})$heterocyclic, and $(C_{4-8})$heteroaryl. Optionally said method, comprises: administering a compound of formula I having an $IC_{50}$ of about 0.0001 to about 50 micromolar for inhibiting a rat bladder muscle strip contraction in vitro; optionally administering a drug selected from the group consisting of a PDE5 inhibitor drug and an antimuscarininc drug; and optionally administering to the bladder directly or intervesiculary an effective amount of a Myosin II ATPase inhibitor compound of formula I, a pharmaceutically-acceptable salt, a racemic mixture, an enantiomer, or a prodrug thereof. Yet further according to the invention, a method of treating an overactive bladder in a patient includes administering to said patient an effective amount of a Myosin II ATPase inhibitor compound of formula (II), or a pharmaceutically-acceptable salt, a racemic mixture, an enantiomer, or a prodrug thereof,

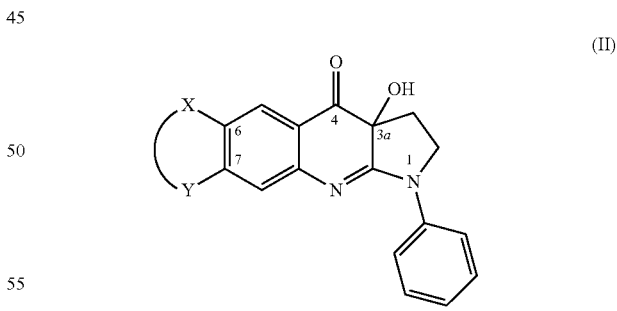

(II)

wherein: X is selected from the group consisting of hydrogen, methyl, hydroxyl, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[(C_{1-6})$alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$, $(C_{1-6})$alkylaminoketo, acetoxy, carb$(C_{1-6})$alkoxy, $(C_{1-6})$alkyl-C(=O)—O—$(C_{1-6})$alkyl, $(C_{1-6})$alkyl-O—C(=O)—$(C_{1-6})$alkyl, acetamido, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenyklalanyl, tyrosinyl, trytophanyl, threoninyl, cystinyl, asparginyl, glutamyl, lysinyl, histidinyl, arginyl, aspartyl, and glutamyl, optionally substituted at a carbon atom with a substituent W, the substituent W selected from the group consisting of methyl, hydroxyl, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino[$(C_{1-6})$alkyl]$_2$, $(C_{1-6})$alkylamino, $(C_{1-6})$alkylamino$(C_{1-6})$alkyl, $(C_{1-6})$alkylamino[$(C_{1-6})$alkyl]$_2$, $(C_{1-6})$alkylaminoketo, acetoxy, carb$(C_{1-6})$alkoxy, $(C_{1-6})$alkyl-C(=O)—O—$(C_{1-6})$alkyl, $(C_{1-6})$alkyl-O—C(=O)—$(C_{1-6})$alkyl, acetamido, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenyklalanyl, tyrosinyl, trytophanyl, threoninyl, cystinyl, asparginyl, glutamyl, lysinyl, histidinyl, arginyl, aspartyl, and glutamyl, and optionally substituted at a primary nitrogen atom or at a secondary nitrogen atom with a substituent Q, the substituent Q selected from the group consisting of methyl, $(C_{1-6})$alkyl, cyclopropyl, $(C_{2-6})$alkenyl, $(C_{2-6})$alkynl, $(C_{1-6})$haloalkyl, $(C_{3-7})$cycloalkyl, $(C_{4-7})$cycloalkenyl, phenyl, benzyl, napthyl, $(C_{4-8})$heterocyclic, $(C_{4-10})$aryl, $(C_{4-10})$haloaryl, and $(C_{4-8})$heteroaryl; wherein Y is selected from the group consisting of hydrogen, methyl, hydroxyl, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino[$(C_{1-6})$alkyl]$_2$, $(C_{1-6})$alkylamino, $(C_{1-6})$alkylamino$(C_{1-6})$alkyl, $(C_{1-6})$alkylamino[$(C_{1-6})$alkyl]$_2$, carbamyl, $(C_{1-6})$alkylaminoketo, acetoxy, carb$(C_{1-6})$alkoxy, $(C_{1-6})$alkyl-C(=O)—O—$(C_{1-6})$alkyl, $(C_{1-6})$alkyl-O—C(=O)—$(C_{1-6})$alkyl, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenyklalanyl, tyrosinyl, trytophanyl, threoninyl, cystinyl, asparginyl, glutamyl, lysinyl, histidinyl, arginyl, aspartyl, and glutamyl, optionally substituted at a carbon atom with a substituent Z, the substituent Z selected from the group consisting of methyl, hydroxyl, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino[$(C_{1-6})$alkyl]$_2$, $(C_{1-6})$alkylamino, $(C_{1-6})$alkylamino$(C_{1-6})$alkyl, $(C_{1-6})$alkylamino[$(C_{1-6})$alkyl]$_2$, carbamyl, $(C_{1-6})$alkylaminoketo, acetoxy, carb$(C_{1-6})$alkoxy, $(C_{1-6})$alkyl-C(=O)—O—$(C_{1-6})$alkyl, $(C_{1-6})$alkyl-O—C(=O)—$(C_{1-6})$alkyl, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenyklalanyl, tyrosinyl, trytophanyl, threoninyl, cystinyl, asparginyl, glutamyl, lysinyl, histidinyl, arginyl, aspartyl, and glutamyl, and optionally substituted at a primary nitrogen atom or at a secondary nitrogen atom with a substituent T, the substituent T selected from the group consisting of methyl, $(C_{1-6})$alkyl, cyclopropyl, $(C_{2-6})$alkenyl, $(C_{2-6})$alkynl, $(C_{1-6})$haloalkyl, $(C_{3-7})$cycloalkyl, $(C_{4-7})$cycloalkenyl, phenyl, benzyl, $(C_{4-10})$aryl, napthyl, $(C_{4-10})$haloaryl, $(C_{4-8})$heterocyclic, and $(C_{4-8})$heteroaryl; and wherein an atom of X and an atom of Y are in a chemical bond that forms a ring from X and Y; wherein said ring is ortho-fused to substituent positions 6 and 7 of a ring of Formula (II). Optionally said method, comprises: administering a compound of formula II having an $IC_{50}$ of about 0.0001 to about 50 micromolar for inhibiting a rat bladder muscle strip contraction in vitro; optionally administering a drug selected from the group consisting of a PDE5 inhibitor drug and an antimuscarininc drug; and optionally administering to the bladder directly or intervesiculary an effective amount of a Myosin II ATPase inhibitor compound of formula II, a pharmaceutically-acceptable salt, a racemic mixture, an enantiomer, or a prodrug thereof.

DETAILED DESCRIPTION OF THE INVENTION

Figure 1:
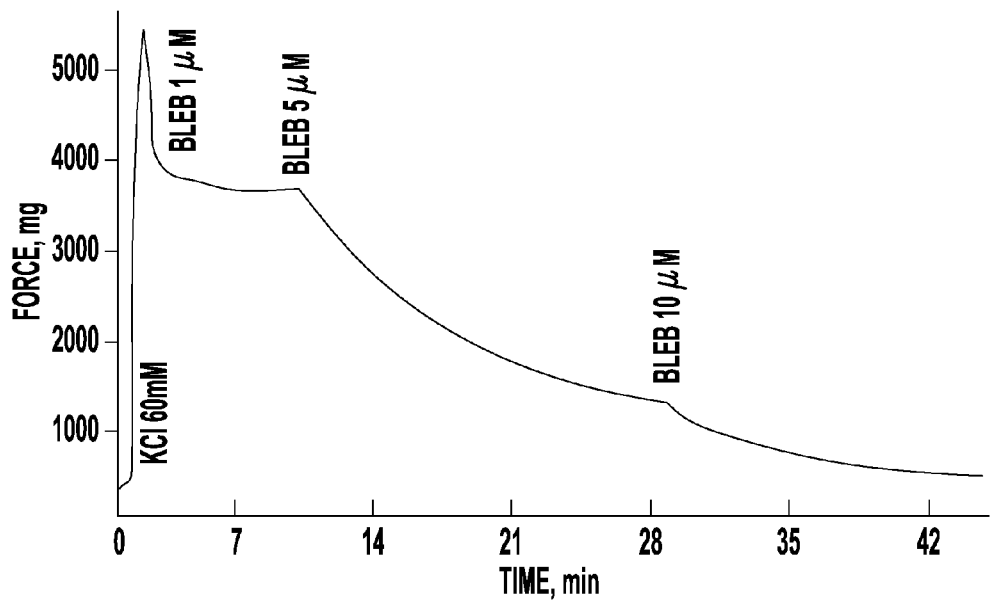
FIG. 1 shows a tracing of the change in tension (contraction) versus time of a rat bladder smooth muscle strip mounted in a tissue bath pre-contracted with 60 millimolar KCL (potassium chloride) and then relaxed using 1 uM, then 5 uM and then 10 uM BLEB. The abbreviation uM means micromolar. The abbreviation BLEB means racemic blebbistatin. A racemic mixture of blebbistatin [(±) of BLEB] was used in all studies unless otherwise noted. The x-axis represents time in minutes (min) while the y-axis represents force (mg). Maximal response to pre-contraction stimulus was taken as 100%, while the relaxant effect of cumulative concentrations (1-10 µM) of BLEB was evaluated as a percentage of this response.

A patient with an overactive bladder (a patient with OAB or an OAB patient) has an increased urge to urinate and less control as to when urination shall occur compared to a normal person. It is an important object of the present invention to provide a therapeutically effective method of treating an overactive bladder in a patient, so that the OAB patient can have a normal degree of voluntarily control their bladder. To be therapeutically effective, the present invention method of treating an overactive bladder in a patient comprises administering to the patient an effective amount of a Myosin II ATPase inhibitor compound.

During experiments for the present invention, it was surprisingly found that the Myosin II ATPase inhibitor blebbistatin reduced tonic and phasic contractions in adult rat bladder smooth muscle strips induced by potassium chloride, carbacol (carbamylcholine), and electric field stimulation. In follow-up OAB animal model experiments for the present invention, a blebbistatin composition was instilled (administered) by a catheter into the over-active bladder of an adult living rat.

Myosin II ATPase is an enzyme associated with the contraction process of smooth muscle. By genetic and chromatographic methods, there are presently four Myosin II ATPase isoforms that have been detected in smooth muscle. The differences in their polypeptide sequences and differences in their conformational structures have unknown consequences. Isoforms of a protein can be produced by related genes, or may arise from the same gene by alternative splicing. Some isoforms are caused by single-nucleotide polymorphisms or SNPs, small genetic differences between alleles of the same gene. SNPs can occur at specific individual nucleotide positions within a gene. In smooth muscle there are at least four slice variants from a single Myosin ATPase gene. In addition to the heavy chains there are 2 light chains and at least four splice variants of the light chains (Aguilar, H. N.: Xiao, S: Knoll, A. H.; Yuan, X (2010) "Physiological pathways and molecular mechanisms regulating uterine contractility" Human Reproduction Update: 16 (6) 725).

Blebbistatin is a small organic molecule with chemical structure name: 3a-hydroxy-6-methyl-1-phenyl-1,2,3,3a-tetrahydro-4H pyrrolo[2,3b]quinolin-4-one, that was discovered by vitro testing for an inhibitor of a non-muscle Myosin II ATPase using $IC_{50}$ measurements as a criteria (Straight A F, Cheung A, Limouze J et al. "Dissecting temporal and spatial control of cytokinesis with a Myosin II Inhibitor" Science 2003; 299: 1743-7). An $IC_{50}$ measurement is a determination of the concentration of an inhibitor that causes a 50% inhibition of a biological process such as an enzyme activity, and the $IC_{50}$ can have units of concentration, such as uM (micromolar). The potency of an inhibitor is inversely-related to its $IC_{50}$ value. The Myosin II ATPase inhibitor, blebbistatin, has been reported to have significantly different $IC_{50}$ values in vitro in different tissues, such as for example, in rabbit striated skeletal muscle bebbistatin inhibits the Myosin II ATPase with an $IC_{50}$ value of 0.5 uM; in pig cardiac muscle bebbistatin inhibits the Myosin II ATPase with an $IC_{50}$ value of 1.2 uM); and in turkey smooth muscle bebbistatin inhibits the Myosin II ATPase with an $IC_{50}$ value of 79.6 uM). (Limouze J, Straight A F, Mitchison T, Sellers J R. "Specificity of blebbistatin, an inhibitor of Myosin II." J Muscle Res Cell Motil 2004; 25:337-41). Furthermore, Ekman et al. reported that 10 uM blebbistatin did not block an adult mouse bladder smooth muscle contraction when the tissue is depolarized using potassium chloride. However, 10 uM blebbistatin did inhibit the bladder contraction of a newborn mouse. The new-born mouse bladder was found to predominantly express a different Myosin II ATPase isoform known as the non-muscle Myosin II ATPase isoform (Ekman M, Fagher K, Wede M, Stakeberg K, Amer A. "Decreased phosphatase activity, increased Ca2+ sensitivity, and myosin light chain phosphorylation in urinary bladder smooth muscle of newborn mice" J Gen Physiol 2005; 125: 187-96).

It was surprisingly found that a pharmaceutical composition of the Myosin ATPase inhibitor blebbistatin, based upon measured urodynamic parameters, reduced the overactivity of the adult rat bladder in vivo. During other contraction experiments on isolated human bladder strips for the present invention it was surprisingly found that the Myosin II ATPase inhibitor blebbistatin completely blocked the strong contraction induced by endothelin-1 in human bladder tissue strips.

In treating an OAB patient, the doctor of an OAB patient can apply experience learned from helping other OAB patients and can refer to clinical and preclinical test reports on the treatment and observation of an OAB patient. Administered to an OAB patient, an effective amount of a Myosin II ATPase inhibitor compound will be observed to reduce the frequency of urination by an OAB patient. One can give an OAB patient beginning treatment for the first time, a small amount of a Myosin II ATPase inhibitor compound and evaluate its clinical effectiveness. Timing and measuring volume of urine collection can be used to determine when the OAB patient is being administered an effective amount of the Myosin II ATPase inhibitor. In addition the OAB patient can inform the doctor about how well the medicine is working, as for example, preferably the frequency of urination by an OAB patient would be reduced so that the patient would not have to wake up more than once during their night time sleep. Secondly, increased voluntary control of urination would be another means for knowing if an effective amount of the Myosin II ATPase inhibitor had been administered. Again the OAB patient can indicate when they believe they are being administered an effective amount of the Myosin II ATPase inhibitor.

The invention provides a method of treating an overactive bladder in a patient, the method comprising administering to the patient an effective amount of a Myosin II ATPase inhibitor compound, useful in its active form, for example comprising a 3a-hydroxy-1-phenyl-1,2,3,3a-tetrahydro-4H pyrrolo[2,3b]quinolin-4-one as represented by structural Formula 1, or a pharmaceutically-acceptable salt, racemic mixture, enantiomer, or prodrug thereof,

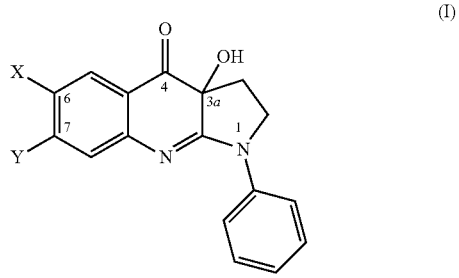

(I)

wherein X is selected from the group consisting of hydrogen, methyl, hydroxy, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[C_{1-6}$)alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$, $(C_{1-6})$alkylaminoketo, acetoxy, carb$(C_{1-6})$alkoxy, $(C_{1-6})$alkyl-C(=O)—O—$(C_{1-6})$alkyl, $(C_{1-6})$alkyl-O—C(=O)—$(C_{1-6})$alkyl, acetamido, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, cyclopropyl, $(C_{3-7})$cycloalkyl, $(C_{4-7})$cycloalkenyl, phenyl, $(C_{4-10})$aryl, napthyl, benzyl, (C4-10)haloaryl, (C4-8)heterocyclic, (C4-8)heteroaryl, glycinyl, alanyl, serinyl, valinyl, leucinyl, isolecinyl, prolinyl, methionyl, phenylalanyl, tyrosinyl, tryptophanyl, threonyl, cystinyl, asparginyl, glutamyl, lysinyl, histidinyl, arginyl, aspartyl, and glutamyl, optionally substituted at a carbon atom with a substituent W, the substituent W selected from the group consisting of methyl, hydroxy, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[C_{1-6})$alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$, $(C_{1-6})$alkylaminoketo, acetoxy, carb$(C_{1-6})$alkoxy, $(C_{1-6})$alkyl-C(=O)—O—$(C_{1-6})$alkyl, $(C_{1-6})$alkyl-O—C(=O)—$(C_{1-6})$alkyl, acetamido, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenylalanyl, tyrosinyl, tryptophanyl, threonyl, cystinyl, asparginyl, glutamyl, lysinyl, histidinyl, arginyl, aspartyl, and glutamyl, optionally substituted at a primary nitrogen atom or at a secondary nitrogen atom with a substituent Q, the substituent Q selected from the group consisting of methyl, $(C_{1-6})$alkyl, cyclopropyl, $(C_{2-6})$alkenyl, $(C_{2-6})$alkynl, $(C_{1-6})$haloalkyl, $(C_{3-7})$cycloalkyl, $(C_{4-7})$cycloalkenyl, phenyl, benzyl, napthyl, $(C_{4-8})$heterocyclic, ($C_{4-10}$)aryl, ($C_{4-10}$)haloaryl, and ($C_{4-8}$)heteroaryl; wherein Y is selected from the group consisting of hydrogen, methyl, hydroxy, fluoro, chloro, bromo, iodo, nitro, cyano, carboxy, carbethoxy, acetyl, ($C_{1-6}$)alkyl, ($C_{2-6}$)alkenyl, ($C_{2-6}$)alkynl, methoxy, ($C_{1-6}$)alkoxy, thio, methylthio, thiomethyl, ($C_{1-6}$)alkylthio, thio($C_{1-6}$)alkyl, chloromethyl, fluoromethyl, trifluoromethyl, ($C_{1-6}$)haloalkyl, ($C_{1-6}$)haloalkoxy, carbamyl, amino, methylamino, aminomethyl, amino($C_{1-6}$)alkyl, amino[$C_{1-6}$]alkyl]$_2$, ($C_{1-6}$)alkylamino, ($C_{1-6}$)alkylamino($C_{1-6}$)alkyl, ($C_{1-6}$)alkylamino[($C_{1-6}$)alkyl]$_2$, carbamyl, ($C_{1-6}$)alkylaminoketo, acetoxy, carb($C_{1-6}$)alkoxy, ($C_{1-6}$)alkyl-C(=O)—O—($C_{1-6}$)alkyl, ($C_{1-6}$)alkyl-O—C(=O)—($C_{1-6}$)alkyl, ($C_{1-6}$)hydroxyalkyl, ($C_{1-6}$)alkylcarboxy, ($C_{1-6}$)alkanoyl, acetonyl, ($C_{1-6}$)alkyl-keto-($C_{1-6}$)alkyl, ($C_{1-6}$)alkoxy($C_{1-6}$)alkyl, acetamido, cyclopropyl, ($C_{3-7}$)cycloalkyl, ($C_{4-7}$)cycloalkenyl, phenyl, ($C_{4-10}$)aryl, napthyl, benzyl, ($C_{4-10}$)haloaryl, ($C_{4-8}$)heterocyclic, ($C_{4-8}$)heteroaryl, glycinyl, alanyl, serinyl, valinyl, leucinyl, isolecinyl, prolinyl, methionyl, phenyklalanyl, tyrosinyl, trytophanyl, threoninyl, cystinyl, asparginyl, glutamyl, lysinyl, histidinyl, arginyl, aspartyl, and glutamyl, optionally substituted at a carbon atom with a substituent Z, the substituent Z selected from the group consisting of methyl, hydroxy, fluoro, chloro, bromo, iodo, nitro, cyano, carboxy, carbethoxy, acetyl, ($C_{1-6}$)alkyl, ($C_{2-6}$)alkenyl, ($C_{2-6}$)alkynl, methoxy, ($C_{1-6}$)alkoxy, thio, methylthio, thiomethyl, ($C_{1-6}$)alkylthio, thio($C_{1-6}$)alkyl, chloromethyl, fluoromethyl, trifluoromethyl, ($C_{1-6}$)haloalkyl, ($C_{1-6}$)haloalkoxy, carbamyl, amino, methylamino, aminomethyl, amino($C_{1-6}$)alkyl, amino[($C_{1-6}$)alkyl]$_2$, ($C_{1-6}$)alkylamino, ($C_{1-6}$)alkylamino($C_{1-6}$)alkyl, ($C_{1-6}$)alkylamino[($C_{1-6}$)alkyl]$_2$, carbamyl, ($C_{1-6}$)alkylaminoketo, acetoxy, carb($C_{1-6}$)alkoxy, ($C_{1-6}$)alkyl-C(=O)—O—($C_{1-6}$)alkyl, ($C_{1-6}$)alkyl-O—C(=O)—($C_{1-6}$)alkyl, ($C_{1-6}$)hydroxyalkyl, ($C_{1-6}$)alkylcarboxy, ($C_{1-6}$)alkanoyl, acetonyl, ($C_{1-6}$)alkyl-keto-($C_{1-6}$)alkyl, ($C_{1-6}$)alkoxy($C_{1-6}$)alkyl, acetamido, cyclopropyl, ($C_{3-7}$)cycloalkyl, ($C_{4-7}$)cycloalkenyl, phenyl, ($C_{4-10}$)aryl, napthyl, benzyl, ($C_{4-10}$)haloaryl, ($C_{4-8}$)heterocyclic, ($C_{4-8}$)heteroaryl, glycinyl, alanyl, serinyl, valinyl, leucinyl, isolecinyl, prolinyl, methionyl, phenyklalanyl, tyrosinyl, trytophanyl, threoninyl, cystinyl, asparginyl, glutamyl, lysinyl, histidinyl, arginyl, aspartyl, and glutamyl, and optionally substituted at a primary nitrogen atom or at a secondary nitrogen atom with a substituent T, the substituent T selected from the group consisting of methyl, ($C_{1-6}$)alkyl, cyclopropyl, ($C_{2-6}$)alkenyl, ($C_{2-6}$)alkynl, ($C_{1-6}$)haloalkyl, ($C_{3-7}$)cycloalkyl, ($C_{4-7}$)cycloalkenyl, phenyl, benzyl, ($C_{4-10}$)aryl, napthyl, ($C_{4-10}$)haloaryl, ($C_{4-8}$)heterocyclic, and ($C_{4-8}$)heteroaryl.

Provided is a test for a formula I or a formula II compound of the present invention. The test allows for a determination of the $IC_{50}$ of the compound for an inhibition of a rat bladder smooth muscle contraction in vitro. The $IC_{50}$ test is described in detail before EXAMPLE 1 of the written description and is entitled "$IC_{50}$ of a Compound of the Invention for Inhibition of Contraction of a Rat Bladder Strip". Also this Test may be referred to herein as a test measuring "inhibition of contraction of rat bladder muscle strip in vitro" and the compound's $IC_{50}$ data may be called "rat bladder strip contraction $IC_{50}$ data".

When a Myosin II ATPase inhibitor compound of formula 1 and of formula II is "in an active form", this means the compound of the invention is active and can inhibit Myosin II ATPase and can be tested in vitro on a rat bladder to determine its $IC_{50}$ for inhibition of a contraction of said bladder. A Myosin II ATPase inhibitor compound of formula 1 and of formula II "in an active form" can have an $IC_{50}$ value between about 0.001 to about 50 micromolar based on inhibiting a contraction of a rat bladder muscle strip in vitro. A Myosin II ATPase inhibitor compound of formula 1 and of formula II in its active form can have an IC50 of about 0.0001 to about 20 micromolar, the IC50 based on inhibiting a rat bladder muscle strip contraction in vitro.

The present invention includes methods of treatment of an overactive bladder of a patient which comprise administering a compound which is a Myosin II ATPase inhibitor, wherein the compound a prodrug. A prodrug of the present invention is a compound which may not be active as an inhibitor of Myosin II ATPase. A compound of the invention in its prodrug form has a chemical group modification. When the chemical group modification is removed from the prodrug, then the compound of the invention may be "in its active form" as an inhibitor of Myosin II ATPase. For example a prodrug of Formula I and II compounds can have an ester group as a chemical group modification, the chemical group modification located as an optional substituent of X or of Y or as a chemical modification group of the hydroxy group located at position 3a of a Formula I or a Formula II compound of the invention. When the ester group no longer present on the compound, then compound may be "in its active form".

Some Myosin II ATPase inhibitor compounds of formula 1 and formula II in their active form have an $IC_{50}$ values between about 0.001 to about 50 micromolar micromolar based on inhibiting a contraction of a rat bladder muscle strip in vitro. Preferably, the Myosin II ATPase inhibitor compounds of formula 1 and formula II in their active form have an $IC_{50}$ values between about 0.001 to about 20 micromolar micromolar based on inhibiting a contraction of a rat bladder muscle strip in vitro; more preferably Myosin II ATPase inhibitor compounds of formula 1 and formula II in their active form, have an $IC_{50}$ values between about 0.001 to about 10 micromolar micromolar based on inhibiting a contraction of a rat bladder muscle strip in vitro; even more preferably the Myosin II ATPase inhibitor compounds of formula 1 and formula II in their active form have an $IC_{50}$ values between about 0.001 to about 5 micromolar micromolar based on inhibiting a contraction of a rat bladder muscle strip in vitro. Most preferred Myosin II ATPase inhibitor compounds of formula 1 and formula II in their active form have a rat bladder strip test $IC_{50}$ values between about 0.001 to about 1.0 micromolar micromolar based on inhibiting a contraction of a rat bladder muscle strip in vitro. The rat bladder muscle strip test can also be useful for testing a conversion of a prodrug of formula I or a prodrug of formula II "to its active form". In addition, the rat bladder strip $IC_{50}$ test can also be used to evaluate or discover a compound's light stability or instability or assess the potency of a metabolite of a compound of the invention as an inhibitor of Myosin II ATPase or as having some other effect, as well as to help discover other chemical changes of a compound of the invention that might alter its rat bladder muscle strip test $IC_{50}$ value.

Provided is a method of treating an overactive bladder in a patient, the method comprising administering to the patient an effective amount of a Myosin II ATPase inhibitor compound, useful in its active form, comprising a 3a-hydroxy-1-phenyl-1,2,3,3a-tetrahydro-4H-pyrrolo[2,3b]quinolin-4-one as represented by structural Formula 1, or a pharmaceutically-acceptable salt, racemic mixture, enantiomer, or prodrug thereof,

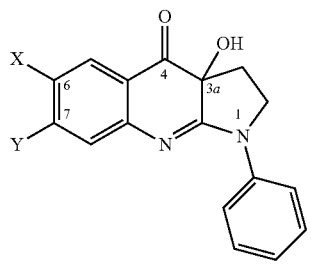

(I)

wherein X is selected from the group consisting of hydrogen, methyl, hydroxy, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[(C_{1-6})$alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$, carbamyl, $(C_{1-6})$alkylaminoketo, acetoxy, carb$(C_{1-6})$alkoxy, $(C_{1-6})$alkyl-C($=$O)—O—$(C_{1-6})$alkyl, $(C_{1-6})$alkyl-O—C($=$O)—$(C_{1-6})$alkyl, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenylalanyl, tyrosinyl, trytophanyl, threonyl, cystinyl, asparginyl, glutamyl, lysinyl, histidinyl, arginyl, aspartyl, and glutamyl, optionally substituted at a carbon atom with a substituent W, the substituent W selected from the group consisting of methyl, hydroxy, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[C_{1-6})$alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$, carbamyl, $(C_{1-6})$alkylaminoketo, acetoxy, carb$(C_{1-6})$alkoxy, $(C_{1-6})$alkyl-C($=$O)—$(C_{1-6})$alkyl, $(C_{1-6})$alkyl-O—C($=$O)—$(C_{1-6})$alkyl, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenylalanyl, tyrosinyl, tryptophanyl, threonyl, cystinyl, asparginyl, glutamyl, lysinyl, histidinyl, arginyl, aspartyl, and glutamyl, optionally substituted at a primary nitrogen atom or at a secondary nitrogen atom with a substituent Q, the substituent Q selected from the group consisting of methyl, $(C_{1-6})$alkyl, cyclopropyl, $(C_{2-6})$alkenyl, $(C_{2-6})$alkynl, $(C_{1-6})$haloalkyl, $(C_{3-7})$cycloalkyl, $(C_{4-7})$cycloalkenyl, phenyl, benzyl, napthyl, $(C_{4-10})$aryl, $(C_{4-10})$haloaryl, $(C_{4-8})$heterocyclic, and $(C_{4-8})$heteroaryl; wherein Y is selected from the group consisting of hydrogen, methyl, hydroxy, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[(C_{1-6})$alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$ $(C_{1-6})$alkylaminoketo, acetoxy, carb$(C_{1-6})$alkoxy, $(C_{1-6})$alkyl-C($=$O)—O—$(C_{1-6})$alkyl, $(C_{1-6})$alkyl-O—C($=$O)—$(C_{1-6})$alkyl, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenylalanyl, tyrosinyl, tryptophanyl, threonyl, cystinyl, asparginyl, glutamyl, lysinyl, histidinyl, arginyl, aspartyl, and glutamyl, optionally substituted at a carbon atom with a substituent Z, the substituent Z selected from the group consisting of methyl, hydroxy, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[(C_{1-6})$alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$, carbamyl, $(C_{1-6})$alkylaminoketo, acetoxy, carb$(C_{1-6})$alkoxy, $(C_{1-6})$alkyl-C($=$O)—O—$(C_{1-6})$alkyl, $(C_{1-6})$alkyl-O—C($=$O)—$(C_{1-6})$alkyl, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenyklalanyl, tyrosinyl, trytophanyl, threoninyl, cystinyl, asparginyl, glutamyl, lysinyl, histidinyl, arginyl, aspartyl, and glutamyl, optionally substituted at a primary nitrogen atom or at a secondary nitrogen atom with a substituent T, the substituent T selected from the group consisting of methyl, $(C_{1-6})$alkyl, cyclopropyl, $(C_{2-6})$alkenyl, $(C_{2-6})$alkynl, $(C_{1-6})$haloalkyl, $(C_{3-7})$cycloalkyl, $(C_{4-7})$cycloalkenyl, phenyl, benzyl, $(C_{4-10})$aryl, napthyl, $(C_{4-10})$haloaryl, $(C_{4-8})$heterocyclic, and $(C_{4-8})$heteroaryl; and wherein said Myosin II ATPase inhibitor compounds of Formula 1, have an $IC_{50}$ value between about 0.001 to about 50 micromolar based on a test of an inhibition of contraction of a rat bladder muscle strip in vitro.

For the present invention, the meaning of a $(C_{1-6})$alkyl includes methyl, ethyl, propyl, isopropyl, butyl, sec-butyl, isobutyl, tert-butyl, pentyl, 2-methylbutyl, isopentyl, tert-pentyl, neopentyl, hexyl, 1-methyl-pentyl, 2-methylpentyl, 3-methylpentyl, isohexyl, tert-hexyl, neohexyl, and 2,2-dimethyl-butyl.

For the present invention, the meaning of a $(C_{2-6})$alkenyl includes (a) a $(C_{2-6})$alkyl minus 2 hydrogens and having 1 carbon double bond; (b) a $(C_{2-6})$alkyl missing 4 hydrogens and having 2, carbon double bonds; and (c) $(C_{2-6})$alkyl missing 6 hydrogens and having 3 carbon double bonds. For the present invention, the meaning of a $(C_{2-6})$alkynyl includes a $(C_{2-6})$alkyl minus 4 hydrogens and having one triple carbon bond.

For the present invention, the meaning of a $(C_{1-6})$haloalkyl includes a $(C_{1-6})$alkyl having one or a plurality of halogen atoms (F, Cl, Br, or I) substituents in place of a hydrogen atom on a carbon atom of the alkyl group.

For the present invention, the meaning of a $(C_{1-6})$alkoxy includes methoxy, ethoxy, propoxy, isopropoxy, butoxy, sec-butoxy, isobutoxy, tert-butoxy, pentoxy, 2-methylbutoxy, isopentoxy, tert-pentoxy, neopentoxy, hexoxy, 1-methylpentoxy, 2-methylpentoxy, 3-methylpentoxy, isohexoxy, tert-hexoxy, neohexoxy, or 2,2-dimethylbutoxy.

For the present invention, the ring group may be fully saturated with hydrogen or have 1-3 double bonds or maximum aromatic ring character as one of skill in organic chemistry would appreciate or understand for any of the fore-mentioned optional substituents based definitive rules for nomenclature of organic chemistry as taught by IUPAC (the International Union of Physics and Chemistry 1957 Rules pages C1-C-73 in the CRC Press Handbook of Chemsistry and Physics, 54th Edition, Cleveland, Ohio) supplemented by the textbook "Organic Chemistry", 6th Edition, Morrison & Boyd, 1992.

For the present invention, a $(C_{3-12})$cycloalkyl means a cyclic alkyl ring of 3 to 12 carbons. Examples include cyclopropyl, cyclobutyl, cyclopentyl, cyclohexyl, cycloheptyl, cyclooctyl, cyclononyl, cyclodecyl.cycloundecyl, and cyclododecyl.

For the present invention, the meaning of a $(C_{4-12})$ cycloalkenyl means a ring with 4 to 12 carbon atoms and includes a double bond or a plurality of double bonds in the ring and includes all contemplated isomers of cyclobutenyl, cyclopentenyl, cyclohexenyl, cycloheptenyl, cyclooctenyl, cyclononenyl, cyclodecenyl.cycloundecenyl, and cyclododecenyl rings.

For the present invention, the meaning of a $(C_{4-12})$ heterocyclic includes a non-aromatic ring system having 4 to 12 atoms in one ring, or in two fused rings, said ring or rings having in total at least one or more carbon atoms replaced by one or more heteroatoms selected from the group consisting of N, O, and S. For the present invention the meaning of a $(C_{4-12})$heterocyclic includes rings such as for example, axiridinyl, oxiranyl, thiiranyl, oxaziridinyl, dioxiranyl, azetidinyl, oxetanyl, thietanyl, diazetanyl, dioxzetanyl, dithietanyl, pyrrolidinyl, tetrahydrofuranyl, imidazolidinyl, pyrazolidinyl, oxazolidinyl, isoxalidinyl, thiazolidinyl, isothiazolidinyl, dioxolanyl, dithiolanyl, piperidinyl, oxanyl, thianyl, piperazinyl, morpholinyl, thiomorpholinyl, dioxanyl, or dithianyl ring. Some $(C_{4-12})$heterocyclic ring examples named to indicate where a bond may be attached include: 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrorolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, 5 diazolonyl, N-substituted diazolonyl, and 1-pthalimidinyl.

For the present invention, the meaning of a $(C_{4-12})$aryl includes a carbocyclic aromatic ring or two rings spiro or fused having 4 to 12 carbon atoms and significant aromatic character. $(C_{4-10})$Aryl examples include cyclobutadiene, cyclopentadiene, pentalenyl, phenyl, indenyl, azulenyl, and naphthyl. Aromatic character in such rings becomes apparent when there are two or more double bonds in each ring.

For the present invention, the meaning of a $(C_{4-12})$ heteroaryl includes one aromatic ring or two aromatic rings arranged in some way or in two fused rings, said ring or rings having in total 4-12 atoms, of which 3-11 are carbon atoms, wherein at least one or more carbon atoms is replaced by a heteroatom selected from the group consisting of N, O, and S. $(C_{4-12})$heteroaryl examples include imidazolyl, isoimidazolyl, thienyl, furanyl, pyridyl, pyrimidyl, pyranyl, pyrazolyl, pyrrolyl, pyrazinyl, thiazolyl, isothiazolyl, oxazolyl, isooxazolyl, 1,2,3-triazolyl, 1,2,4-triazolyl, and tetrazolyl. benzofuranyl, isobenzofuranyl, pyrrolyl, indolyl, isoindolyl, thiophenyl, benzothiophenyl, benzo[b]thienyl, benzo[c]thiophenyl, imidazoyl, oxazolyl, benzoxazoyl, isoxazoyl, benzisoxazoyl, thiazoyl, benzothiazolyl, pyridinyl, quinolinyl, isoquinolinyl, pyrazinyl, quinoxalinyl, acridinyl, pyrimidinyl, and cinnolinyl.

(S)-blebbistatin, (−)-blebbistatin, (−)-(S)-blebbistatin, and racemic-blebbistatin are some of the preferred compounds of the present invention. A racemic mixture of blebbistatin enantiomers has useful potent Myosin II ATPase inhibitory activity. An (S)-enantiomer or an (−)-enantiomer of blebbistatin or another compound of the invention can be a potent Myosin II ATPase inhibitor also as a racemic mixture with its corresponding (R)-enantiomer or (+)-enantiomer.

(R)-blebbistatin has a much higher IC50 value than (S)-blebbistatin. Thus (R)-blebbistatin can be used as a "control" during in vitro bladdr smooth muscle contraction studies of the inhibitory effects of (S)-blebbistatin or racemic blebbistatin.

For the present invention note that blebbistatin can be named in a variety of ways. The names (−)-blebbistatin, (S)-blebbistatin and (S)-(−)-blebbistatin refer to the same enantiomer of the same compound (Lucas-Lopez, C., Patterson, S, Blum, T., Straight, A. F., Toth, J., Slawin, A. M. Z., Mitchison, T. J., Sellers and, J. R., Westwood, N. J. "Absolute Stereochemical Assignment and Fluorescence Tuning of the Small Molecule Tool, (−)-Blebbistatin" *European J. Organic Chemistry*. (2005), pp 1736-1740.). IUPAC (International Union of Physicists and Chemists) publications state a preference in chemical naming of a compound that the chemical name list its group substituents in an alphabetic order with the core ring system last named if the ring system is selected as the core molecule from which there are the group substituents. Accordingly (S)-blebbistsatin is named (S)-3aS-hydroxy-6-methyl-1-phenyl-1,2,3,3a-tetrahydro-4H-pyrrolo[2,3b]quinolin-4-one). Also accordingly then (−)-blebbistatin is named (−)-3aS-hydroxy-6-methyl-1-phenyl-1,2,3,3a-tetrahydro-4H-pyrrollo[2,3b]quinolin-4-one). However (S)-blebbistatin might be named (S)-6-methyl-1-phenyl-1,2,3,3a-tetrahydro-3aS-hydroxy-4H-pyrrolo[2,3b]quinolin-4-one). Also (−)-blebbistatin might be named (−)-6-methyl-1-phenyl-1,2,3,3a-tetrahydro-3aS-hydroxy-4H-pyrrolo[2,3b]quinolin-4-one). For the present invention, these names for the (−) enantiomer of blebbistatin should be considered to mean the same enantiomer of blebbistatin.

Synthesis of Formula 1 and Formula II compounds of the present invention can use intermediate organic chemical compounds and chemical reagents, the later reagents are easily purchased. The substituted intermediate organic chemical compounds such as the substituted anthranilic acid esters intermediate compounds, can now be bought as well or custom made by some chemical companies and purchased for making a compound of the present invention. Said intermediate organic chemical compounds can be made or bought and optionally may be used in a form having a chemical blocking groups ("protecting groups") that protects some of the compound's group substituents during a synthetic chemical reaction.

When buying an intermediate chemical compound for the present invention, there are several approaches to select from. One approach is to use the chemical database and pharmaceutical building block resources at Maybridge.com to obtain the internmediate compound. A second approach is to use MolPort.com, a website resource that enables a centralized ordering of chemical compounds from over 200 chemical companies and provides a database of commercially available chemical compounds. A third approach is to contact and then buy the intermediate chemical compounds and fine reagents from the Sigma-Aldrich Chemical Company (St. Louis, Mo., U.S.), Molport Chemical Company (Riga, Latvia), or Thermo-Fisher-Scientific subsidiary Maybridge Chemical Company in the U.S. or in Tintigal, U.K. The compound or its intermediate may be synthetically prepared in a custom batch order by contacting Maybridge Chemical Company service CustomBlocks™ (link is maybridge.sales at Thermofisher.com) a subsidiary of Thermo Fisher Scientific Inc. The third approach which is working with Maybridge Chemical Company is a preferred means for obtaining complex intermediates of a compound of the invention.

A compound of formula I or formula II of the present invention or for that matter any chemical structure for a compound that inhibits or may conceivably inhibit Myosin II ATPase, can be written out on paper as a molecular structure. Optionally said molecular structure can be sent to a chemical company such as Maybridge Chemical Company for its custom synthesis for a fee. Thus, it is contemplated for the present invention, that a compound of the invention that may be a Myosin II ATPase inhibitor can be conceived, and then can be custom-made by a chemical company as a means for enabling one of skill in the art to practice any aspect of the present invention as needed.

One of ordinary skill in the art of organic chemical synthesis will appreciate that the synthesis of the Myosin II ATPase compounds of the present invention is facilitated when performed by an experienced Ph.D. organic chemist having a resourceful, careful, and safety-conscious set of skills and who has been working in medicinal drug discovery at a pharmaceutical company or university for several years in heterocyclic organic chemicals synthesis. Said chemist will have experience in purchasing and effectively using various intermediate organic compounds from chemical supply companies. Said chemist will select a specific (−)-3aS-hydroxy-quinolone compound 5 to be made. Then, using a disclosed synthetic route of the present invention, said chemist will know each specific chemical compound intermediate in the synthetic route making the formula I and formula II compounds of the present invention.

To one of skill in organic synthesis, some synthetic routes to compounds of the present invention will be more efficiently performed using "protecting groups" (also known as "blocking groups") on the intermediate compounds. Protecting groups are well known in the art of organic chemical synthesis as a means for increasing the selectivity of an organic chemical reaction. Selective chemical reactions are known to enable a higher purity and higher yield reaction product, advantageously facilitating subsequent reactions. It is an object of the present invention that synthesis of the compounds of formula I and formula II are well-controlled so that only the unprotected chemical group substitutents in the intermediates react in each reaction step. An alcohol, amine, carbonyl, carboxylic, phosphate, or terminal alkyne groups may need to be chemically-blocked before a reaction step to keep them from participating in the reaction.

Protection of alcohols can be done using a blocking group for protection of alcohol groups selected from the group consisting of acetyl (Ac), benzoyl (Bz), benzyl (Bn, Bnl), β-methoxyethoxymethyl ether (MEM), dimethoxytrityl, [bis-(4-methoxyphenyl)phenylmethyl] (DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), Trityl (triphenylmethyl, Tr), Silyl ether, trimethylsilyl ether (TMS), tert-butyldimethylsilyl ether (TBDMS), tri-iso-propylsilyloxymethyl ether (TOM), triisopropylsilyl ether (TIPS), methyl ethers (ME), and ethoxethyl ethers (EE).

The alcohol protecting groups are removed in different ways. An acetyl group is removed by acid or base. A benzoyl group is removed by acid or base, more stable than Ac group. A benzyl group is removed by hydrogenolysis. A β-Methoxyethoxymethyl ether group is removed by acid. A dimethoxytrityl group is removed by weak acid. A methoxymethyl ether group is removed by acid. A methoxytrityl group is removed by acid and hydrogenolysis. A p-methoxybenzyl ether group is removed by acid, hydrogenolysis, or oxidation. A methylthiomethyl ether group is removed by acid. A pivaloyl group is removed by acid, base or reducing agents. A pivalyl group is substantially more stable than other acyl protecting groups. A tetrahydropyranyl group is removed by acid. Trityl is removed by acid and hydrogenolysis. A silyl ether group such as TMS, TBDMS, TOM, and TIPS, are removed by acid or fluoride ion (such as NaF, TBAF (Tetra-n-butylammonium fluoride, HF-Py, or HF-NEt3)). A methyl ether group is cleaved by TMSI in dichloromethane, acetonitrile, or chloroform; alternatively cleave silyl ethers using $BBr_3$ in Dichloromethane. An ethoxyethyl ethers group can be cleaved in 1N HCl.

Protection of amines can be done using a blocking group for protection of amine groups selected from the group consisting of (1) carbobenzyloxy (Cbz), (2) p-methoxybenzyl carbonyl (Moz or MeOZ), (3) tert-butyloxycarbonyl (BOC), (4) 9-fluorenylmethyloxycarbonyl (FMOC), (5) acetyl (Ac), (6) benzoyl (Bz), (7) benzyl (Bn), (8) carbamate, (9) p-methoxybenzyl (PMB), (10) 3,4-dimethoxybenzyl (DMPM), (11) p-methoxyphenyl (PMP), (12) tosyl (Ts) and other sulfonamides (Nosyl & Nps).

The amine protecting groups are removed in different ways. A carbobenzyloxy group is removed by hydrogenolysis. A p-methoxybenzyl carbonyl group is removed by hydrogenolysis. It is more labile than a Cbz group. A tert-butyloxycarbonyl group is removed by concentrated, strong acid. (such as HCl or $CF_3COOH$). A 9 fluorenylmethyloxycarbonyl group is removed by a base, such as piperidine. An acetyl group is removed by treatment with a base, most often, with aqueous or gaseous ammonia or methylamine. An acetyl group is too stable to be readily removed from aliphatic amides. A benzoyl group is removed by treatment with a base, most often with aqueous or gaseous ammonia or methylamine. A benzoyl like an acetyl group is too stable to be readily removed from aliphatic amides. A benzyl group is removed by hydrogenolysis. A carbamate group is removed by acid and mild heating. A p-methoxybenzyl group is removed by hydrogenolysis, and is more labile than a benzyl group. A 3,4-dimethoxybenzyl group is removed by hydrogenolysis, and is more labile than a p-methoxybenzyl group. A p-methoxyphenyl group is removed by Ammonium cerium(IV) nitrate. A tosyl group is removed by concentrated acid such as HBr or $H_2SO_4$; or by a strong reducing agent such as sodium in liquid ammonia or sodium naphthalenide. Other sulfonamides such as Nosyl and Nps can be removed by samarium iodide or tributyltin hydride.

Protection of carbonyl groups can be done using a carbonyl blocking group selected from the group consisting of (1) acetals and ketals (which are removed by acid and cleavage of an acyclic acetals is easier than a cleavage of a cyclic acetal), (2) acylals (which are removed by a Lewis acid), and (3) dithianes which are removed by metal salts or oxidizing agents.

Protection of carboxylic acid groups can be done using a carboxyl blocking group selected from the group consisting of (1) methyl esters (which are removed by acid or base), (2) benzyl esters (which are removed by hydrogenolysis), (3) tent-butyl esters (which are removed by acid, base and some reducing agents), (4) silyl esters (which are removed by acid, base and organometallic reagents), (5) orthoesters (which are removed by mild aqueous acid to form an ester, said ester then removed with a facility depending on its ester properties), and (6) oxazoline (which is removed by strong hot acid with a pH<1 and at a temperature above 100° C. or which is removed by alkali creating pH greater than 12 and at a temperature above 100° C.), but said blocking group does not protect against LiAlH$_4$, organolithium reagents or Grignard (organomagnesium) reagents.

Protection of phosphate groups can be done using a phosphate blocking group selected from the group consisting of (1) 2-cyanoethyl (which is removed by mild base), and (2) methyl (which removed by a strong nucleophiles such as a mixture of thiophenol with triethanolamine).

Protection of a terminal alkyn group can be done using a terminal alkyn blocking group selected from the group consisting of (1) propargyl alcohols in the Favorskii reaction, and (2) silyl groups, especially in protection of the acetylene itself.

For example a chemist can select a specific (–)-3aS-hydroxy-quinolone compound 5 of the present invention to be make. Based on knowledge about the use of protecting groups and using a disclosed synthetic route of the present invention, a chemist can make reasonable expectations as to what each chemical intermediate will need to be in the synthetic route that makes the formula I and formula II compounds of the present invention. For example, the methyl anthranilate intermediate compound 2 (depicted below in a reaction scheme diagram) has an X substituent at the five position and a Y substituent at the six position. When the X and the Y substituent groups are free of any "protecting group", then these X and Y correspond to the X and Y disclosed in Formula I and Formula II compounds of the present invention. Thus, below the intermediate compound 2 which is a methyl anthranilate (2-amino-benzoic acid methyl ester) is chosen to provide specific X and Y substituents. As mentioned said intermediate compound 2 may be bought, made by the chemist, or bought custom-made from a company.

For example a synthesis route for a Formula 1 compound comprises making the corresponding intermediate amidine compound 3 by a Step (a) process. Phosphorus oxychloride (POCl$_3$, 1.0 mmol (millimole) is added, drop-wise, to a solution of N-phenyl-2-pyrollidinone 1 (1.1 mmol) in dry dichloromethane (5.0-15 ml [milliliters]) with stirring for 3 hours at room temperature (22° C.). A solution of 1.1 mmol anthranilate 2 in dry dichloromethane (15-60 ml) then is added. The mixture is refluxed for 16-80 hours, is cooled and then is concentrated under vacuum. The solid is dissolved in 0.30 N hydrochloric acid (100 ml) and is extracted with diclormethane (3×100 ml). Then to the aqueous phase is added 100 ml ethyl acetate and slowly using aqueous 2 molar sodium hydroxide, the pH is raised to pH 8.0. The aqueous phase is further extracted with ethyl acetate (3×100 ml). All ethyl acetate extracts are combined and dried with anhydrous MgSO$_4$. The dried ethyl acetate extracts which hold the product as a base, are dried by vacuum to yield amidine solid 3. The process of a Step (a) reaction scheme is below depicted:

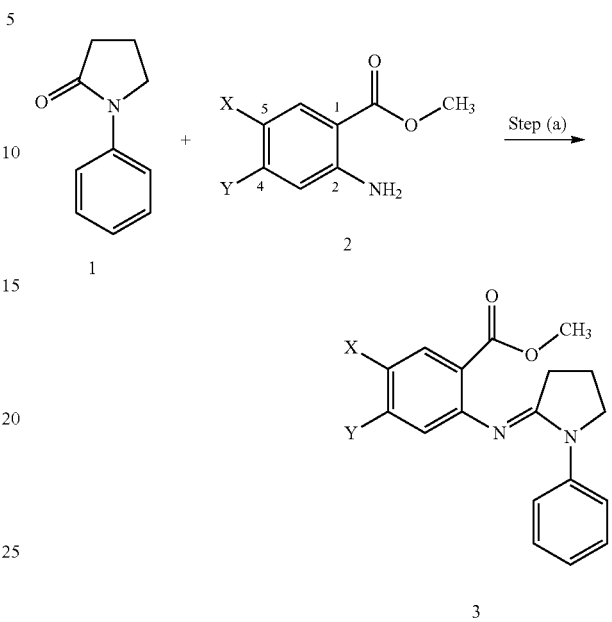

For example, a synthesis route for a Formula 1 compound comprises making the corresponding intermediate quinolone compound 4 by a Step (b) process. A reaction flask holding a solution of the amidine 3 (1.0 mmol) in 50 ml anhydrous THF (tetrahydrofuran is cooled to –78° C. (reaction flask is cooled in acetone/dry ice mix) and is stirred for 15 minutes. A solution of lithium bis(trimethylsilyl)amide (LiHMDS) in THF (1 molar, 3.0 mmol) is added drop-wise to the amidine in THF solution to react. The reaction mixture is allowed to warm to 0° C. over 3 hours or allowed to warm to 22° C. (room temp.) over 12 hours. The reaction is then quenched with saturated aqueous ammonium chloride (150 ml) and the aqueous phase is extracted with dichloromethane (4×100 ml), the CH$_2$Cl$_2$ extracts are combined and are dried using anhydrous magnesium sulfate. After filtering, the anhydrous extract is concentrated by vacuum. The quinolone 4 is purified by flash column chromatography on silica gel eluting with (50-100% ethyl acetate—PE 40-60 [wherein PE 40-60 is the fraction of light petroleum ether boiling in the range of 40-60° C.]). The process of a Step (b) reaction scheme is below depicted.

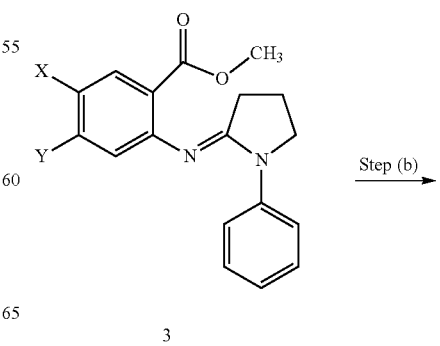

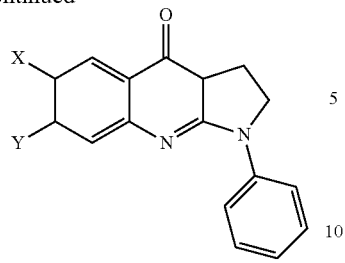

4

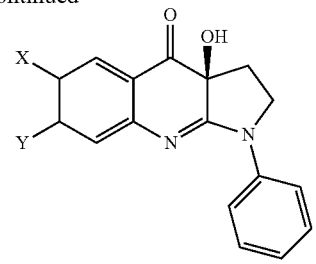

5

For example, a synthesis route for a (−) enantiomer Formula 1 compound by Step (c1) process forms a (−)-3aS-hydroxy-quinolone compound 5. Quinolone 4 (1.0 mmol) in dry THF (10-50 ml) as a solution is added drop-wise to lithium bis(trimethylsilyl)-amide (LiHMDS) in THF (1.0 molar, 1.2 equiv.) in dry THF (2.0-7.0 ml) at −78° C. (reaction flask is cooled in acetone/dry ice mix) under argon. Mixture is stirred (for 30 min.) at −78° C. In dry THF (4-12 ml), 2.4 mmoles of (−)-(8,8-dichlorocamphorylsulfonyl)oxaziridine [Davis oxaziridine method] in solution is added via a cannula. After 16 hours reaction time-mixing at −10° C., a saturated aqueous ammonium iodide solution (5.0 ml, 10 mmol) and diethyl ether (5.0-10 ml) are added. Then the mixture is then extracted with diethyl ether (3×10 ml). Combined organic extracts are dried with magnesium sulfate, filtered and concentrated using a vacuum. The concentrate is added to 100 ml dichloro methane and 100 ml of hydrochloric acid (0.3 molar). The product is now a salt in the aqueous phase portion. The aqueous phase is isolated and washed with CH$_2$Cl$_2$ (3×100 ml). Then the aqueous extract is slowly alkalinized, with aqueous 2.0 molar sodium hydroxide until the pH is 8.0. The product, now a base, is suspended in the aqueous phase, said aqueous phase then extracted with ethyl acetate (3×100 ml). Combined ethyl acetate extracts are dried with magnesium sulfate, filtered, an concentrated to obtain the base product which is substantially the (−) enantiomer, namely, (−)-3aS-hydroxy -quinolone compound 5. For the present invention compound 5 can also be called a (−)-6-X,7-Y-substituted Formula 1 compound, and also can be called a(−)aS -hydroxy-1-phenyl-6-X,7-Y-1,2,3,3a-tetrahydro-4H-pyrrollo[2,3b] quinolin-4-one). Step (c1) reaction scheme depicted below.

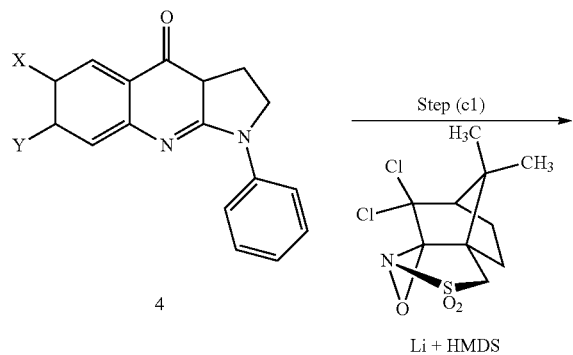

For example, optionally, a (−)-3aS-hydroxy-quinolone compound 5 can be recrystallized in acetonitrile or a similar solvent, using standard recrystallization methods of one of skill in the art, to increase its enantiomeric purity from below 90% E.E. to about 99.5% E.E. as needed. The E.E. % values are determined using chiral HPLC. In addition, a compound of the present invention will exist in different polymorph forms. Polymorphs can have advantages such as improved solubility, improved chemical stability, and improve a characteristic of or the process of making a pharmaceutical formulation. The present invention includes any polymorphs of intermediates, and of compounds of formula I and formula II.

For example, using above described synthetic routes for making 1 millimole of (−)-blebbistatin and starting with 5-methyl anthranilate methyl ester 1 (X=CH$_3$, Y=H), a 41% yield has been reported for the formation of the corresponding amidine 3; a 90% yield has been reported for the cyclization of amidine 3 to quinolone 4; an 82% yield has been reported for 3a-hydroxylation of quinolone 4 to (−)-3a-hydroxy-quinolone 5, said (−)-3a-hydroxy-quinolone 5 compound has been reported to have an enantiomeric excess of 82% (E.E. 82%); and following a single crystallization in a solvent such as acetonitrile, said (−)-3a-hydroxy-quinolone 5 compound has been reported to have an optical purity of 99.5% E.E. [(1) Lucas-Lopez, C., Allingham, J S., Lebl, T., Lawson, C. P. A. T., Brenk, R., Sellers, J. R., Rayment, I., Westwood, N. J. "The small molecule tool (S)-(−)-blebbistatin: novel insights of relevance to myosin inhibitor design" *Organic & Biomolecular Chemistry* (2008); vol. 6:pp 2076-2084. (2) Lucas-Lopez, C., Patterson, S, Blum, T., Straight, A. F., Toth, J., Slawin, A. M. Z., Mitchison, T. J., Sellers and, J. R., Westwood, N. J. "Absolute Stereochemical Assignment and Fluorescence Tuning of the Small Molecule Tool, (−)-Blebbistatin" *European J. Organic Chemistry*. (2005), pp 1736-1740. (3) Patterson, S., Lucas-Lopez, C., Westwood, N. J. "Selective Chemical Interventions in Biological Systems: The Small Molecule Tool, (S)-(−)-Blebbistatin" pp 147-166, *Beilstein-Institute, The Chemical Theatre of Biological Systems*, (May 24th-28th, 2004) Bozen, Italy.]

For example, a synthesis of (±) racemic Formula 1 compounds: (−)-3aS-hydroxy-quinolone compound 5 and (+)-3aR-hydroxy-quinolone compound 6 from racemic hydroxylation of carbon 3a in quinolone compound 4 is shown in Step (c2) below. Quinolone compound 4 is racemically hydroxylated at carbon 3a when dissolved in dimethylsulfoxide (DMSO) or in THF and the solution is exposed to air. The rate and yield of the racemic 3a carbon hydroxylation of quinolone compound 4 is increased by irradiation of said solution of compound 4 by a medium pressure mercury lamp (400 watt, or upon irradiation at 368 nanometers of the compound on silica gel. A 3 hour exposure to the mercury lamp at 25° C., gives a yield of 26% in DMSO and a yield of 29% in THF for making a racemic mixture of the 3aR- and 3aS-hydroxy-quinolone compound 5 (specifically, (±)-blebbistatin, has been reported (Lucas-Lopez, C., Patterson, S, Blum, T., Straight, A. F., Toth, J., Slawin, A. M. Z., Mitchison, T. J., Sellers and, J. R., Westwood, N. J. "Absolute Stereochemical Assignment and Fluorescence Tuning of the Small Molecule Tool, (−)-Blebbistatin" European J. Organic Chemistry. (2005), pp 1736-1740.). Step (c2) racemic reaction scheme is depicted below which forms both hydroxyl 3a enantiomers from quinolone intermediate compound cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[(C_{1-6})$alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$, $(C_{1-6})$alkylaminoketo, acetoxy, carb$(C_{1-6})$alkoxy, $(C_{1-6})$alkyl-C(=O)—O—$(C_{1-6})$alkyl, $(C_{1-6})$alkyl-O—C(=O)—$(C_{1-6})$alkyl, acetamido, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, cyclopropyl, $(C_{3-7})$cycloalkyl, $(C_{4-7})$cycloalkenyl, phenyl, $(C_{4-10})$aryl, napthyl,

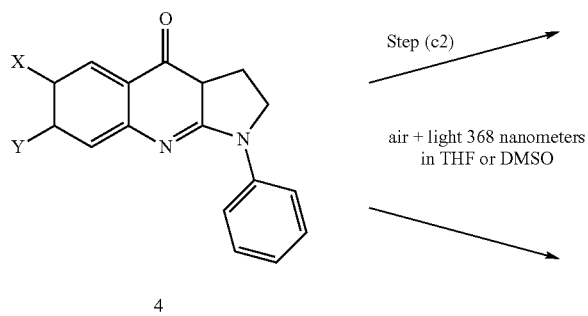

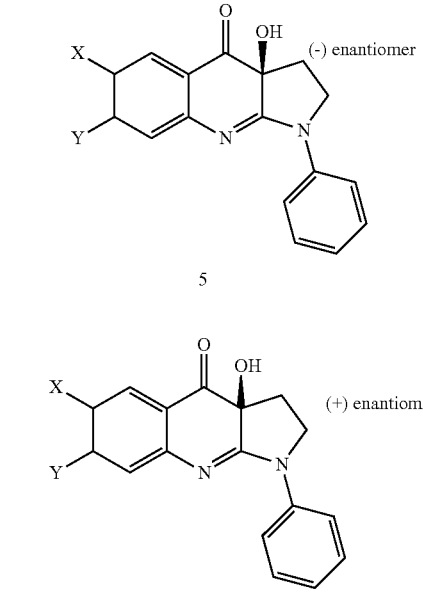

A third embodiment of the invention provides a method of treating an overactive bladder in a patient, the method comprising administering to the patient an effective amount of a Myosin II ATPase inhibitor compound, useful in its active form, comprising a substituted 3a-hydroxy-1-phenyl-1,2,3,3a-tetrahydro-4H-pyrrolo [2,3b] quinolin-4-one as represented by structural Formula II, or a pharmaceutically-acceptable salt, racemic mixture, enantiomer, or prodrug thereof,

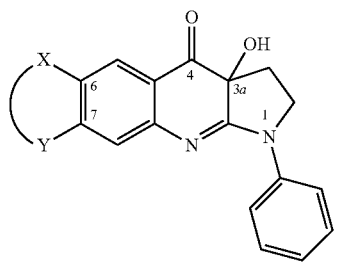

wherein X is selected from the group consisting of hydrogen, methyl, hydroxy, fluoro, chloro, bromo, iodo, nitro, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenyklalanyl, tyrosinyl, trytophanyl, threoninyl, cystinyl, asparginyl, glutamyl, lysinyl, histidinyl, arginyl, aspartyl, and glutamyl, optionally substituted at a carbon atom with a substituent W, the substituent W selected from the group consisting of methyl, hydroxy, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[(C_{1-6})$alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$ $(C_{1-6})$alkylaminoketo, acetoxy, carb$(C_{1-6})$alkoxy, $(C_{1-6})$alkyl-C(=O)—O—$(C_{1-6})$ alkyl, $(C_{1-6})$alkyl-O—C(=O)—$(C_{1-6})$alkyl, acetamido, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$ alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenylalanyl, tyrosinyl, tryptophanyl, threonyl, cystinyl, asparginyl, glutamyl, lysinyl, histidinyl, arginyl, aspartyl, and glutamyl, and optionally substituted at a primary nitrogen atom or at a secondary nitrogen atom with a substituent Q, the substituent Q selected from the group consisting of methyl, $(C_{1-6})$alkyl, cyclopropyl, $(C_{2-6})$alkenyl, $(C_{2-6})$alkynl, $(C_{1-6})$haloalkyl, $(C_{3-7})$cycloalkyl, $(C_{4-7})$cycloalkenyl, phenyl, benzyl, napthyl, $(C_{4-8})$heterocyclic, $(C_{4-10})$aryl, $(C_{4-10})$haloaryl, and $(C_{4-8})$heteroaryl; wherein Y is selected from the group consisting of hydrogen, methyl, hydroxy, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[(C_{1-6})$alkyl$]_2$, $(C_{1-6})$alkylamino, $(C_{1-6})$alkylamino$(C_{1-6})$alkyl, $(C_{1-6})$alkylamino$[(C_{1-6})$alkyl$]_2$, carbamyl, $(C_{1-6})$alkylaminoketo, acetoxy, carb$(C_{1-6})$alkoxy, $(C_{1-6})$alkyl-C(=O)—O—$(C_{1-6})$alkyl, $(C_{1-6})$alkyl-O—C(=O)—$(C_{1-6})$alkyl, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenylalanyl, tyrosinyl, tryptophanyl, threonyl, cystinyl, asparginyl, glutamyl, lysinyl, histidinyl, arginyl, aspartyl, and glutamyl, optionally substituted at a carbon atom with a substituent Z, the substituent Z selected from the group consisting of methyl, hydroxy, fluoro, chloro, bromo, iodo, nitro, cyano, carboxy, carbethoxy, acetyl, $(C_{1-6})$alkyl, $(C_{2-6})$alkenyl, $(C_{2-6})$alkynl, methoxy, $(C_{1-6})$alkoxy, thio, methylthio, thiomethyl, $(C_{1-6})$alkylthio, thio$(C_{1-6})$alkyl, chloromethyl, fluoromethyl, trifluoromethyl, $(C_{1-6})$haloalkyl, $(C_{1-6})$haloalkoxy, carbamyl, amino, methylamino, aminomethyl, amino$(C_{1-6})$alkyl, amino$[C_{1-6})$alkyl$]_2$, $(C_{1-6})$alkylamino, $(C_{1-6})$alkylamino$(C_{1-6})$alkyl, $(C_{1-6})$alkylamino$[C_{1-6})$alkyl$]_2$, carbamyl, $(C_{1-6})$alkylaminoketo, acetoxy, carb$(C_{1-6})$alkoxy, $(C_{1-6})$alkyl-C(=O)—O—$(C_{1-6})$alkyl, $(C_{1-6})$alkyl-O—C(=O)—$(C_{1-6})$alkyl, $(C_{1-6})$hydroxyalkyl, $(C_{1-6})$alkylcarboxy, $(C_{1-6})$alkanoyl, acetonyl, $(C_{1-6})$alkyl-keto-$(C_{1-6})$alkyl, $(C_{1-6})$alkoxy$(C_{1-6})$alkyl, acetamido, cyclopropyl, $(C_{3-7})$cycloalkyl, $(C_{4-7})$cycloalkenyl, phenyl, $(C_{4-10})$aryl, napthyl, benzyl, $(C_{4-10})$haloaryl, $(C_{4-8})$heterocyclic, $(C_{4-8})$heteroaryl, glycinyl, alanyl, serinyl, valinyl, leucinyl, isolecinyl, prolinyl, methionyl, phenylalanyl, tyrosinyl, tryptophanyl, threonyl, cystinyl, asparginyl, glutamyl, lysinyl, histidinyl, arginyl, aspartyl, and glutamyl, and optionally substituted at a primary nitrogen atom or at a secondary nitrogen atom with a substituent T, the substituent T selected from the group consisting of methyl, $(C_{1-6})$alkyl, cyclopropyl, $(C_{2-6})$alkenyl, $(C_{2-6})$alkynl, $(C_{1-6})$haloalkyl, $(C_{3-7})$cycloalkyl, $(C_{4-7})$cycloalkenyl, phenyl, benzyl, $(C_{4-10})$aryl, napthyl, $(C_{4-10})$haloaryl, $(C_{4-8})$heterocyclic, and $(C_{4-8})$heteroaryl; and wherein an atom from X is proximal to an atom of Y and said atoms form a chemical bond; said chemical bond forms a ring from X and Y; wherein the ring is an ortho-fused to an existing ring of Formula II having X and Y.

The invention also provides pharmaceutical compositions comprising an effective amount of a Myosin II ATPase inhibitor compound, useful in its active form, as a method of treating an overactive bladder in a patient. The compounds of the invention comprise optionally substituted compounds and their pharmaceutically-acceptable salts; said pharmaceutically-acceptable salts are well known in the art. Compounds of the present invention may be formulated as salts using an acid to improve the aqueous solubility of the compound. Compounds of the present invention are ionized in acidic solutions which ionized compound is more water soluble. Suitable pharmaceutical salts of the compounds of the present invention include the hydrochloride, sulfate, acetate, phosphate, maleate, citrate, nitrate, tosylate, mesylate and besylate salts. Preferably the salt is a chloride, acetate, sulfate, nitrate, or citrate or besylate salt; or most preferably a chloride salt. There is a tertiary amine at the 1 position in the pyrrole ring and at the 1 position of the quinolin-4-one ring in Formula 1. Thus at least 1 to 2 or more molar equivalents of an acid are needed to protonate the basic Formula 1 compound to form its salt forms. Prodrug formulations of the invention include esters of the Formula I and II compounds that are formed by reacting a 3a-hydroxyl group of the formual I or Formula II compound with acetic acid, benzoic acid or another suitable carboxylic acid to make the corresponding acetate or benzoate or other suitable carboxylic acid ester. The 3a-hydroxy group of a compound of formula I and of formula II of the present invention is essential for the compound to be in "its active form". Compounds of Formula I and II with a chemically modified group such as an ester instead of a hydroxyl at position 3a will be not be "in an active form" as a Myosin II ATPase inhibitor of the invention.

One of skill in the art of organic chemical molecule synthesis methods can use known blocking groups, nucleophilic substitution reactions and addition organic chemistry reactions in various combinations to synthesize the substituted (S)-(−)-blebbistatins of the present invention. Useful synthesis procedures and guidances for the synthesis of racemic and enantiomeric compounds of the present invention may be found also in the following articles: (1) Lucas-Lopez, C., Allingham, J. S., Lebl, T., Lawson, C. P. A. T., Brenk, R., Sellers, J. R., Rayment, I., Westwood, N. J. "The small molecule tool (S)-(−)-blebbistatin: novel insights of relevance to myosin inhibitor design" Org. Biomol. Chem. 2008; 6:2076-2084; (2) Patterson, S., Lucas-Lopez, C., Westwood, N. J. "Selective Chemical Interventions in Biological Systems: The Small Molecule Tool, (S)-(−)-Blebbistatin" pp 147-166, Beilstein-Institute, The Chemical Theatre of Biological Systems, May 24TH,-28TH, Bozen, Italy; and (3) Lucas-Lopez, C, Patterson, S., Blum, T., Straight, A. F., Toth, J., Slawin, A. M. Z., Mitchison, T. J., Sellersand, J. R., Westwood, N. J. "Absolute Stereochemical Assignment and Fluorescence Tuning of the Small Molecule Tool, (−)-Blebbistatin" Eur. J. Org. Chem. 2005, 1736-1740.

For the present invention, many routes of administering of a compound of the present invention are contemplated as a method of treating an overactive bladder of a patient. The drug may be in the form of a base, or a pharmaceutically acceptable salt. The drug may be formulated with conventional excipients whose selection is within ordinary skill in the art of using pharmaceutical excipients to make a pharmaceutical formulation. The design of a formulation is well-known in the art to be modified to accommodate a particular route of administration. Routes of administration for the present invention shall include conventional and non-conventional routes. A preferred route of administration of a Myosin II ATPase inhibitor compound minimizes subjecting a patient being treated for OAB from possible systemic side effects of the compound. A preferred route of administration is direct administration of a Myosin II ATPase inhibitor to the overactive bladder of the patient. The inhibitor compound may be vesicularly administered by any suitable means such as by a cannula or a pump.

Pharmaceutical compositions of the present invention may contain up to 85 wt % of a compound of the invention.

More typically, the pharmaceutical composition contains up to 50% weight of a compound of the invention. Preferred pharmaceutical compositions are sterile and pyrogen free. Preferably the pharmaceutical compositions provided by the invention contain a compound of the invention which is a substantially compound such as a pure (−) optical isomer, a racemic mixture, or a prodrug of a compound of the invention. A therapeutically effective amount of a compound of the invention, its racemic mixture, an enantiomer, or prodrug thereof, that is administered to an OAB patient is about 0.01 mgs to about 50 mg per kg of body weight, depending upon the activity of the compound. Some other factors may guide in selecting the pharmaceutical dose, including the age, weight and conditions of the patient to be treated, the type and severity of the disease and the frequency and route of administration.

Solutions for injection or infusion may contain as carrier, for example, sterile water or preferably they may be in the form of sterile, aqueous, isotonic saline solutions. Preferably a dose of a compound of the invention is administered intervesicularly. Intervesicular administration means administration into the bladder where urine is stored, said urine storage space known as intervesicular space of the bladder.

When for example, a dose of a compound of the invention is administered intervesicularly, then the $IC_{50}$ of the compound in its active form can be useful number to use in estimating a therapeutically effective dose (amount) of the compound to be administered as a treatment of an overactive bladder of a patient, said $IC_{50}$ determined from (a) an in vitro study of the inhibition of adult rat bladder Myosin II ATPase activity or (b) an in vitro study of the inhibition of a human bladder Mysin II ATPase activity or (c) an in vitro study of the inhibition of a adult rat bladder muscle strip contraction. The $IC_{50}$ of the compound in its active form determined from the in vitro study of the inhibition of a adult rat bladder muscle strip contraction is described in detail in the written description of the present invention.

An effective intervesicular dose can be achieved if the intervesicular urine concentration of the compound of the invention is adjusted to between about 0.1 $IC_{50}$ to about 3 $IC_{50}$ of the compound, preferably about 0.5 to about 2.0 $IC_{50}$, of the compound more preferably about 0.80 to about 1.5 $IC_{50}$. of the compound. Most preferably the intervesicular urinary concentration of the compound is equivalent to about 1.0 $IC_{50}$ of the compound of the invention, and if the $IC_{50}$ of the compound is 1 micromolar to 20 to micromolar, then the desired urinary concentration of the compound in its active form would be about 1 to 10 micromolar. A pharmaceutical solution for intervesicular instillation can be designed accordingly, optionally including an adjustment of the dose assuming a dilution effect of the dose by the urine in the bladder.

The $IC_{50}$ of compounds of the invention are typically between 0.0001 micromolar to 50 micromolar and accordingly for said compounds, then the desired urinary concentration of the compound in its active form would be between about 0.0001 micromolar to about 50 micromolar. Compounds having an $IC_{50}$ greater than 50 micromolar may be too impotent and non-selective whereas compounds having an $IC_{50}$ less than 0.0001 may disadvantageously function as an irreversible inhibitor as if covalently-linked irreversibly to the Myosin ATPase. Optionally, the method of treating on overactive bladder of a patient includes between about 0.01 to about 3 $IC_{50}$ of a phosphodiesterase five inhibitor compound, preferably a PDE5 inhibitor such a sildenafil citrate, tadalafil or vardenafil. The $IC_{50}$ of the PDE5 inhibitor may be determined by in vitro test methods known in the art or from published values for the PDE5 inhibitor or from the FDA approved package insert of the available PDE5 inhibitor.

For oral or parenteral administration a compound of the invention may be formulated for administration with a pharmaceutically acceptable carrier or diluent For example, solid oral forms may contain, together with the active compound, diluents, e.g. lactose, dextrose, saccharose, cellulose, corn starch or potato starch lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Light-sensitive compounds of the invention, such as blebbistatin, must be shielded from light. Said compounds in pharmaceutical formulations will have light protection barriers, for example a suitable dye and opacifier excipient in oral formulations, or light-shielding storage and administration containers for a parenteral, i.v., or intervesicular formulation. Optionally a compound of the invention is substituted at the 7 position, if a formula 1 with a nitro group to reduce light sensitivity which causes the compound to become less active or inactivated.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

For the present invention, a preferred route of administration of the medication to treat OAB is a direct route to minimize side effects of the medication. Medication for the present invention is a drug or mixture of drugs comprising a compound of the present invention, the compound may be for example blebbistatin or an "other drug" as "other drug" is defined for the present invention. "Other drug" is a group of chemical substances or drugs which include a smooth muscle relaxant known or to be discovered or a prodrug of a metabolite.

Preferably the medication is deposited into the intravesical space of the bladder (the chamber of the chamber) and remains there a long time so that the treatment of a patient's OAB condition does not require frequent drug administration to the patient. For the present invention, formulations of the medication in the bladder may exist in a reservoir of a small pump ("a drug storing-pumping device") that slowly delivers the drug into the bladder, the pump and reservoir subsiding inside the bladder itself. The device may be placed inside the bladder by a surgical means, by a syringe, or via a cannula. Slow-release formulation preferably would be delivered via the ureter. Advantageously, placement of the drug into the bladder reduces its metabolism, systemic side effects, requires a lower dose, provides faster onset and higher drug levels in the urine (optimizes pharmacokinetics). Another preferable route of administration via the ureter comprises a liquid formulation, a suspension or formulation capable of forming a viscous gel with or without slow time release pellets. Such administration is readily accomplished by a pressure injection involving a cannula in the ureter or urethra, or by pressing a blunted syringe cannula tip into a ureter or urethra so that a non-voidable paste within the bladder may be injected via the ureter under pressure. Optionally, a slowly biodegradable, viscous or sticky pharmaceutical formulations of the present invention can be useful for its ability to adhere to an interior wall of the bladder as needed so the drug is not flushed away when the bladder is emptied during urination.

A patient with OAB may need a temporary or chronic treatment for OAB and a direct administration of a medication comprising a compound of the present invention, the compound may be for example blebbistatin, with or without an "other drug" is an embodiment of the present invention and this embodiment includes a direct instillation or deposition into the intravesical space of the bladder in the form of an immediate release with or without a portion of the formulation performing a slow-release of the medication.

Optionally, for the present invention, the intra-bladder chamber medication delivery can occur via a small pumping device drawing medication from a drug reservoir containing a formulation capable of being pumped at a controlled rate from the reservoir into the bladder chamber wherein pump device and reservoir of drug is located already in the bladder chamber or outside the bladder (Fraser, M. O., Lavelle, J. P., Sacks, M. S., Chancellor, M. B. "The future of Bladder Control-Intravesical Drug Delivery, a Pinch of Peper, and Gene Theraphy" Rev. Urol. 2002; 4(1), pp 1-11).

The medication to treat OAB comprises a compound of the present invention, the compound may be for example blebbistatin, optionally with an "other drug" in a suitable solution, semisolid, powder, foam, gel, slowly forming gel, powder, slow-release formulation of the medication, optionally wherein the medication comprises a pharmaceutically acceptable salt, ester, or prodrug, complex, suspension, or suppository. Optionally the formulation is form or size or condition that prevents its elimination during urination or micturition.

Examples of routes of administration of a medication of the present invention include the following route and any other well-known in the art, for example: (1) an oral route as a tablet, capsule, solution, paste, or spray; (2) a parenteral route as an intravenous injection, a subcutaneous injection, an intramuscular injection, or a muscle depot; (3) a surgically installed inside the body anywhere may be a storage device pump which selectively delivers a pharmaceutical composition solution of a compound of the present invention by an osmotic means, by a compression means, a cannula means, or by diffusion means; (4) a nasal inhalation route as a spray; a transdermal patch route, a rectal suppository as a semisolid, solid or liquid solution; (5) a subcutaneous, parenteral muscle depot or directly introduced into the bladder via a cannula or injection or any other means of direct introduction of said drug into the bladder.

Preferably a pharmaceutical composition of the present invention is administered into the bladder lumen or intervesicular as a solution or introduced therein as a formulation capable of functioning as a slow-drug release formulation. Optionally to minimize urinary losses of the entire drug dose consequent to urination, the formulation of any kind of rate of release, the formulation can be designed to adhere in part to a portion of the bladder wall or lumen, the formulation containing biologically-compatible adhesive molecules known in the art of pharmaceutical excipients with adhesive qualities.

The scope of the present invention includes methods of administering a medication as a therapeutic pharmaceutical means for assisting in the relaxation of a patient's bladder smooth muscle for treating OAB (over-active bladder). Smooth muscle relaxants known in the art may be used as the "other drug". This invention also relates to pharmaceutical compositions comprising said compounds and optionally another drug ("the other drug") or a plurality of other drugs ("the other drugs") and methods of treating a lower urinary tract dysfunction using the same. The present invention is a method of treating a lower urinary tract dysfunction using a Myosin ATPase inhibitor compound and optionally, with an "other drug"(s), or an enantiomer, a pro-drug, a tautomer, a polymorph or a pharmaceutically acceptable salt thereof, said method of treatment advantageously having a reduced side effect or an improved therapeutic effectiveness, or an improved patient compliance in taking their medication for the treatment of their lower urinary tract treatment dysfunction(s).

The present invention includes methods of administering an "other drug" as a means for providing a therapeutic pharmaceutical for treating a patient with OAB. The other drug when combined with blebbistatin or another Myosin II ATPase inhibitor may have additive, and preferably synergistic effects. By treating an overactive bladder with two different drug therapies, such as (a) a Myosin II ATPase inhibitor and (b) an "other drug", the dose of each can be lower, advantageously reducing potential side-effects and reducing a development of metabolic tolerance and a functional tolerance to the medications.

The "other drug" may be a drug known or that will be discovered to modulate smooth muscle contractility, tonus or phasic tension, or relaxation process biochemical pathways. Such modulation may arise when the "other drug" affects levels of cellular cyclic AMP or cyclic GMP, alters levels of synthesis or release of nitric oxide, carbon monoxide, hydrogen sulfide, oxygen, or carbon dioxide in and about bladder smooth muscle cells and tissue. The "other drug" may reduce calcium ion influx into smooth muscle cells, reducing calcium release or storage from smooth muscle intracellular organelles which may play a role in causing calcium ion release or storage by intracellular organelle including endoplasmic reticulum, sarcoplasmic reticulum, mitochondria, calcium binding proteins such a calmodulin or the cell membrane ("glycocalax") or other cellular membranes. The "other drug" may affect Na/Ca exchange; may block calcium channels; may increase or reduce sodium ion efflux/influx; may modulate the IP3 pathway; modulate prostaglandin synthesis; modulate G proteins. The "other drug" may be a cholinergic antagonist such as a muscarinic or nictotinic anatagonist or induce increased levels of an acetylcholinesterase enzyme or an adrenergic antagonist, an inducer of levels of a catechol-o-methyl transferase or a monoamine oxidase or blocker of acetylcholine synthesis or of neuronal release of acetylcholine near smooth muscle cells. The "other drug" may reduce the duration or magnitude of smooth muscle cell membrane depolarization to effect smooth muscle relaxation.

Racemic or (−)-blebbistatin or another Myosin II ATPase inhibitor of the present invention when administered at the same time or having an effect in the same time period as an "other drug", regardless of whether same or separate pharmaceutical formulations, may surprisingly and advantageously reduce the dosage by each drug needed for inducing smooth muscle relaxation as well as prolonging the therapeutic duration of smooth muscle relaxation while beneficially reducing side effects that either drug alone administered may cause. For the present invention method of treating an overactive bladder of a patient, the method may include administering a bladder smooth muscle relaxing agent.

A preferred compound of formula I for the present invention is racemic or (−)-blebbistatin or a Formula 1 or Formula II compound of the present invention. Said compound may be formulated alone or in combination with an "other drug" in a pharmaceutical formulation. The "other drug" may be a phosphodiesterase enzyme inhibitor (PDEI). During formation of cyclic AMP or cyclic GMP, a PDEI prevents breakdown of the cyclic monophosphate nucleotide thereby the smooth muscle cytoplasmic cyclic nucleotide levels (i.e., cyclic AMP or cyclic GMP levels) rise higher and last longer, facilitating and prolonging smooth muscle relaxation. The PDEIs include cyclic GMP PDEI and cyclic AMP PDEI inhibitors. More than 20 phosphodiesterase enzymes (PDE) are known and named PDE1 to PDE20. The distribution of PDEs differs in different cells and organs. The present invention's "other drug" may be a selective inhibitor of one or more of the following phosphodiesterase enzymes: PDE1, PDE2, PDE3, PDE4, PDE5, PDE6, PDE7, PDE8, PDE9, PDE10, PDE11, or PDE12. More preferably the "other drug" is a selective inhibitor of PDE1, PDE4 or PDE5. Most preferably the "other drug" is a selective inhibitor of PDE5. Preferred "other drug:" selective PDE5 inhibitors include sildenafil citrate, vardenafil, or tadalifil which slow hydrolysis of cyclic GMP formed by the nitric oxide signaling pathway. Most preferably, when the "other drug" is a PFE5 inhibitor, then the "other drug" is vardenafil. Examples relatively nonselective PDE inhibitors include caffeine, theophylline, milrinone, and pentoxifylline which inhibit more than one type of PDE and thereby stabilize elevations in cyclic GMP or cyclic AMP in smooth muscle cells depending upon whether CAMP or cGMP is being formed.

The term $IC_{50}$ applied to PDE inhibitor study means the concentration of a PDE inhibitor (PDEI) that causes a 50% inhibition of the PDE's activity by whatever assay means that the IC50 is determined. For example, PDE5 selective inhibitor has a lower $IC_{50}$ for its selected target, PDE5, than for its non-selected target PDE4. The selectivity of a PDE inhibitor is preferably greater than about 10, more preferably greater than about 100, and most preferably greater than about 1000. A potent PDE inhibitor typically will have an $IC_{50}$ less than about 10 micromolar, preferably less than about 1 micromolar, more preferably less than 0.1 micromolar, and most preferably less than 0.01 micromolar.

For the present invention, an administration of a compound of the invention, the compound may be for example, blebbistatin, from the inside chamber of the bladder is an effective means for relaxing a bladder smooth muscle of a patient in order to treat OAB. As shown in FIG. 7B, blebbistatin can reduce both the baseline tone and peak phasic contraction. Preferably the bladder's resting or peak phasic contraction are reduced by the treatment with a compound of the invention, the compound may be for example, blebbistatin, and optionally along with the "other drug" by between about 5 to about 100 percent, to between about 15 to about 100 percent, to between about 25 to 100 percent, preferably to between about 25 to about 90 percent, more preferably to between about 40 to about 80 percent, most preferably to between about 50 to about 75 percent.

Figure 3:
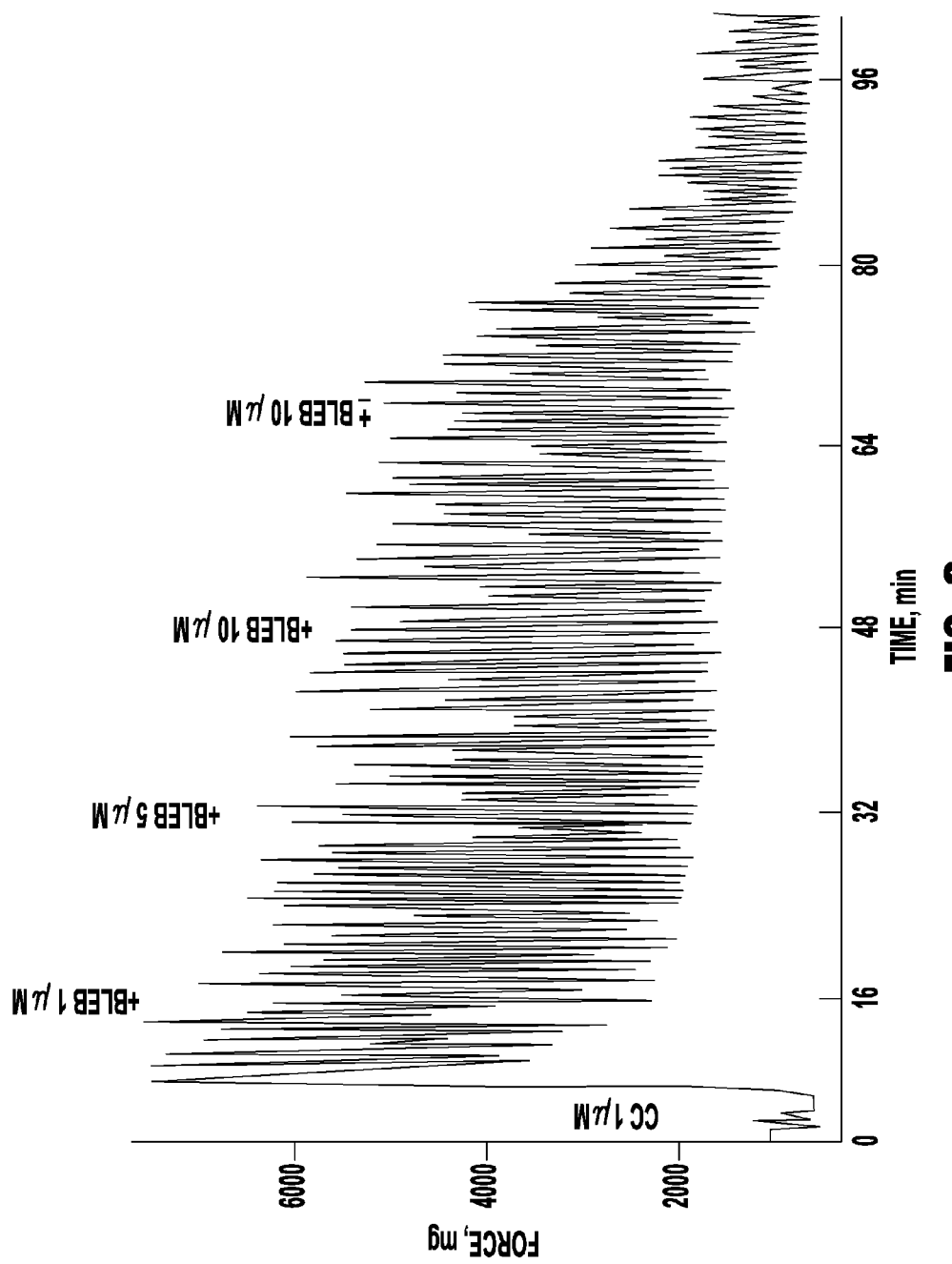
FIG. 3 shows a tracing of the change in tension (contraction) versus time of a spontaneously slowly contracting rat bladder smooth muscle strip mounted in a tissue bath pre-contracted with 1 uM carbacol (CC) which increased its baseline tension and the magnitude of its phasic contractions. The rat bladder smooth muscle strip was then exposed to 1 uM (+)BLE, then 5 uM (+BLE), 10 uM (+)BLE. Here the abbreviation (+)BLE and the abbreviation (+) BLEB shall both mean the (+)-blebbistatin or (R)-blebbistatin enantiomer. The rat bladder smooth muscle strip was then exposed to 10 uM (±) BLE. Here the abbreviation (±) BLE and the abbreviation (±) BLEB shall both mean racemic blebbistatin which can be written as (±)-blebbistatin. Racemic blebbistatin caused a significant decrease in both the baseline and peak phasic force of contraction. The enantiomer (+)-blebbistatin is relatively low potency (has a very high IC50) as an inhibitor of Myosin ATPase and was used as Control in some experiments of the present invention. The x-axis represents time in minutes (min) while the y-axis represents force (mg). Maximal response to pre-contraction stimulus was taken as 100%, while the relaxant effect of cumulative concentrations of 1-10 uM (+) BLE and 10 uM (±) BLE was evaluated as a percentage of this response.
Figure 5A:
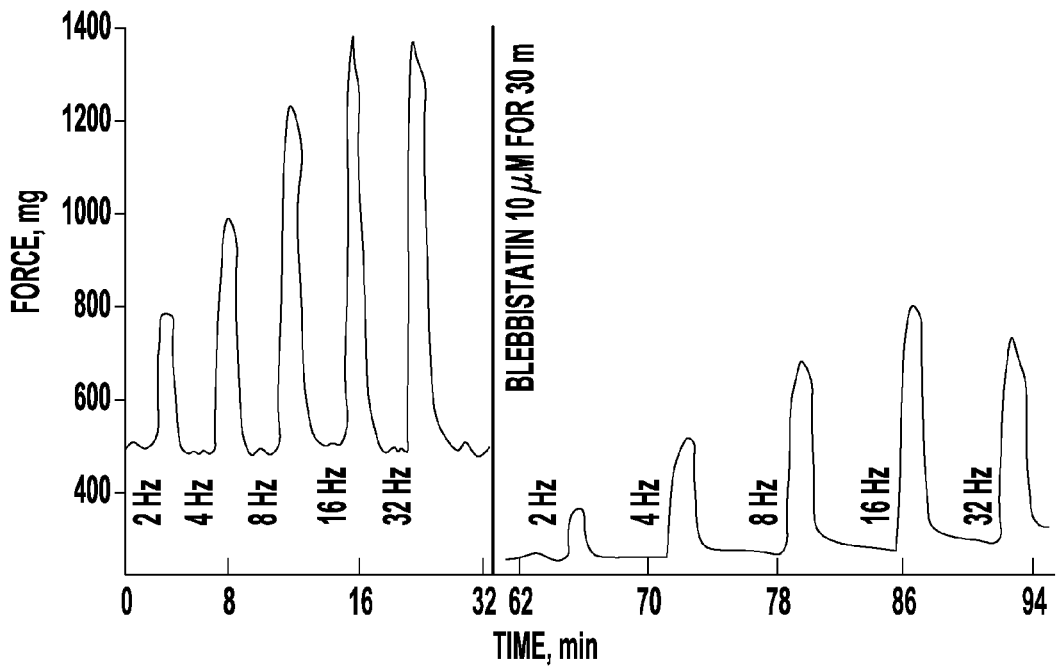
FIG. 5A shows the tension (contraction) development and relaxation versus time of a rat bladder smooth muscle strip mounted in a tissue bath and pre-contracted with 60 mM KCl, during episodes of increasing electric field stimulation (EFS) frequency (2 Hz to 4 Hz, to 8 Hz and to 16 Hz). Hz is an abbreviation for Hertz which means frequency in cycles/second. After several washes without drug to return tension to the basal state, then the detrusor muscle (bladder smooth muscle) was pre-incubated with 10 µM BLEB (racemic blebbistatin) for 30 minutes (min) and then the EFS protocol was repeated.
Figure 7A:
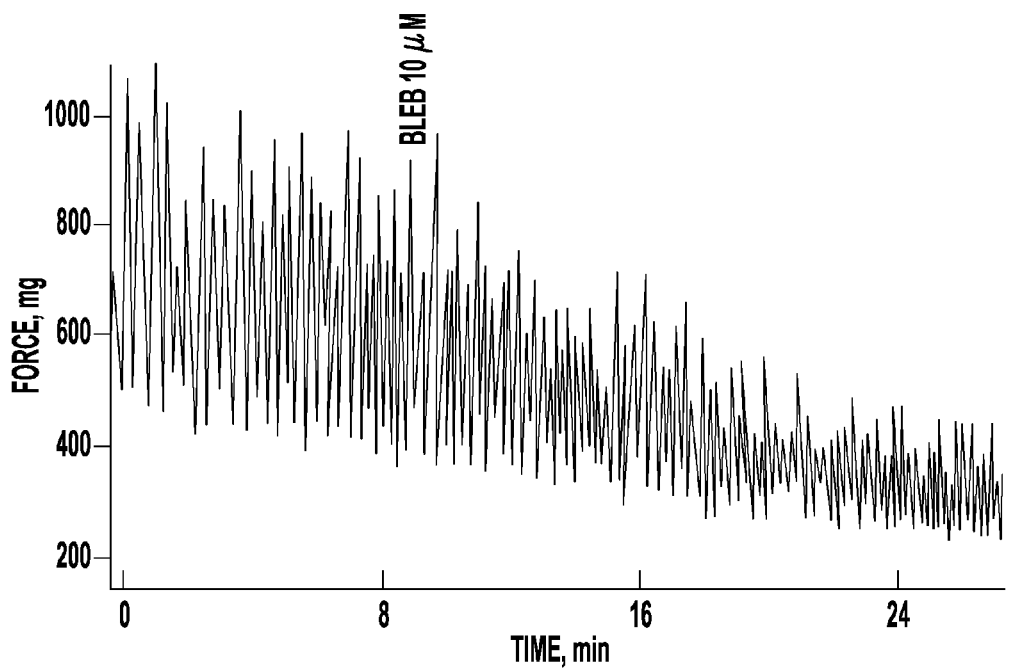
FIG. 7A shows an extended time tracing of spontaneous contraction activity versus time of rat bladder strips mounted in a tissue bath and then 10 µM BLEB (racemic blebbistatin) was added and observed for 60 minutes. The x-axis represents time in minutes (min) while the y-axis represents force (mg). The x-axis represents time (seconds) while the y-axis represents force (mg).
Figure 7B:
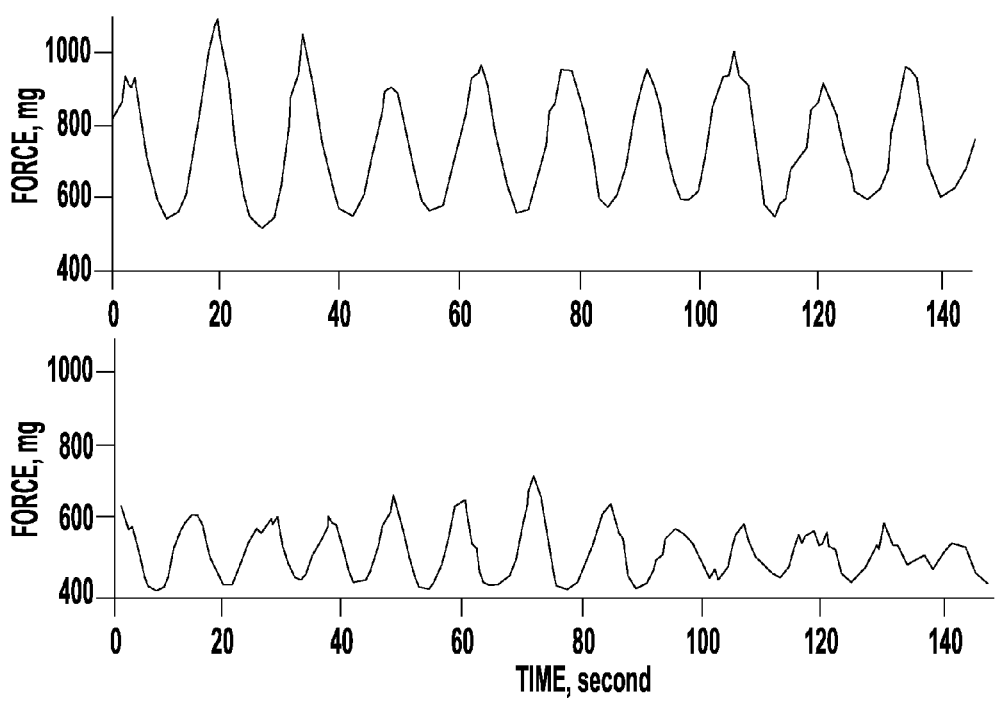
FIG. 7B shows zoomed in tracings of spontaneous contraction activity versus time of rat bladder strips mounted in a tissue bath and then 10 µM BLEB (racemic blebbistatin) was added and observed for 60 minutes. The x-axis represents time in minutes (min) while the y-axis represents force (mg). The x-axis represents time (seconds) while the y-axis represents force (mg). before BLEB treatment while lower panel is after treatment.

It is unexpected that a drug of the present invention reduces spasmodic bladder activity as evident in FIG. 3, FIG. 7A and FIG. 7B. When the bladder is in a contractile state induced by membrane depolarization using 60 mM potassium chloride (KCl) as shown in FIG. 1, or is transiently contracted by electric field stimulation (EFS) at frequencies of 2 Hz to 16 Hz as in FIG. 5A, blebbistatin is an effective and useful means for inhibiting the contractility of the bladder. Similarly when a bladder is contracted by carbacol, the bladder smooth muscle can still be relaxed by blebbistatin.

The efficacy of the present invention to relax a contracted bladder is surprising in view of the fact that an adult mouse bladder does not relax when treated with blebbistatin whereas the rat bladder does relax when exposed to blebbistatin.

$IC_{50}$ of a Compound of the Invention for Inhibition of Contraction of a Rat Bladder Strip:

The in vitro $IC_{50}$ determination for a compound of the invention is based on a test measuring the inhibition of a contraction by an adult rat isolated bladder muscle strip. Said test uses of rat bladder smooth muscle strips is performed in the dark in a tissue chamber apparatus, optionally illuminated with a low intensity red lamp, since some compounds of the invention are known to be light-sensitive to blue to purple or shorter wavelengths of light radiation.

Preferably, eight of the bladder muscle strips are employed in vitro in a first type of inhibition testing. Preferably, eight other bladder muscle strips are employed in a second type of inhibition testing. The muscles strips for each of the test types are obtained, one strip each from eight animals, the animals being Sprague-Dawley rats of 300-375 gram weight and purchased from Charles River Laboratories in the United States. A mean $IC_{50}$ determination per test compound per test type is based on experimental data from 8 muscle test strips In the first type of inhibition testing, the muscle strip in vitro bathed in a physiological saline for an hour as defined in the present detailed description and then contracted with 1 micromolar (uM) carbacol (carbamylcholine), in the saline in a dark tissue chamber, which peak tension takes about 10 minutes. Representative 1 uM carbacol contraction data are in FIG. 2. Several concentrations of the test compound are added in increasing concentrations. For example, the present invention tested 1 uM, 5 uM, and 10 uM racemic blebbistatin. The magnitude of a muscle strip contraction is measured when the magnitude is appears to have reached a stable point which may take 10-40 minutes of test compound exposure. One of ordinary skill in the art knows a mean $IC_{50}$ can be calculated from such type one test data.

In the second test type, the muscle strip contractions can triggered using about 4 to 6 minutes of electric field stimulation (EFS) at frequencies of 2, 4, 8, 16, and 32 as shown in FIG. 3. Then the EFS contractions are repeated in the presence of increasing concentrations of the test compound. A test result is shown in FIG. 3 for testing with 10 uM racemic blebbistatin. One of ordinary skill in the art knows an $IC_{50}$ can be calculated from such type two test data. The overall $IC_{50}$ of a test compound defined as a calculated value midway between the type one test mean measured $IC_{50}$ and the type two test mean measured $IC_{50}$. Said defined overall $IC_{50}$ value is a test compound's functional rat bladder contractility $IC_{50}$ for the present invention. It is intended for the present invention that for each test compound, its overall functional rat bladder contractility $IC_{50}$ being defined can be systematically useful in a number of ways, including (a) to compare the potency of two test compounds, (b) to discovery a useful compound of the present invention and (c) to conduct infringement or anticipation by a compound. Further details of such $IC_{50}$ determinations are taught in the detailed description.

Detailed methods for studying in vitro changes in the contractility of rat bladder smooth muscle caused by a Myosin II ATPase inhibitor, such as blebbistatin, may be found in Zhang, X, Kuppam, D S R, Melman, A, DiSanto, M E. "In vitro and In vivo relaxation of urinary bladder smooth muscle by the selective Myosin II inhibitor, blebbistatin" BJU Internat. e-publication 2010, journal publication, 2011; Volume 107, Issue 2, pages 310-317.

EXAMPLE 1

In Vitro Test Response of Rat Bladder and Human Bladder Smooth Muscle Strip to Blebbistatin 17 male Sprague Dawley rats along with multiple human bladder smooth muscle strips obtained from an open prostatectomy were used for racemic blebbistatin organ bath studies. Awake cystometry was performed on a separate set of 5 rats in both the presence and absence of intravesically delivered racemic blebbistatin. The effect of racemic blebbistatin on pharmacologically and nerve-mediated bladder SM contraction was determined. The influence of racemic blebbistatin on urodynamic properties was also assessed. Results: Racemic blebbistatin completely relaxed both KCl and carbachol induced rat detrusor and endothelin-1 induced human bladder (limited to base) contraction in a dose-dependent manner. Pre-incubation with 10 µM racemic blebbistatin attenuated carbachol responsiveness by ~65% while blocking electrical field stimulation-induced bladder contraction reaching 50% inhibition at 32 Hz. Basal tone and amplitude of spontaneous contraction were also significantly blunted. Urodynamic parameters, consistent with OAB, were obviously ameliorated by racemic blebbistatin intravesical infusion. The novel data of the present invention establish that racemic blebbistatin potently strongly relaxes both rat and human bladder contraction induced by various physiological agonists. In vivo tests showed that nanomolar doses of racemic blebbistatin significantly alter urodynamic parameters to a less active bladder.

Experimental materials and methods: All chemical were from Sigma (St. Louis, USA) except (±) blebbistatin (racemic blebbistatin) was from Tocris (Ellisville, Mo.). A stock solution of racemic blebbistatin was made in DMSO (dimethylsulphoxide; the other substances were dissolved daily in double distilled water. Control experiments showed that the final concentrations (1/1000-3/1000) of DMSO used in these studies did not significantly modify the relaxation response induced by racemic blebbistatin. Due to the known light sensitivity of blebbistatin, it was always kept in the dark in the refrigerator until just prior to usage. During the experiment, the organ bath chambers were covered. Human bladder (base) samples were obtained from simple open benign prostatectomy surgery with informed consent and approval of the Institutional Review Boards of Montefiore Medical Center and the Albert Einstein College of Medicine. Rat bladder body and aorta were obtained from 17 (275-300 gram) adult male Sprague-Dawley (SD) rats (Charles River; Raleigh, N.C.). All animal studies were approved by the Animal Institute Committee of the Albert Einstein College of Medicine.

It was determined that the active (−) enantiomer form of blebbistatin was equipotent to the racemic blebbistatin mixture in the in vitro studies and that the inactive (+) enantiomer form of blebbistatin form did not induce significant bladder relaxation.

In vitro organ bath studies: The in vitro contractility studies were performed as previously described by Zhang X, Kuppam D, Aydin M, Melman A, DiSanto M. "In vitro and in vivo relaxation of corpus cavernosum smooth muscle by the selective myosin II inhibitor, blebbistatin." J Sex Med 2009; 6:2661-71, Sandhu K S, Chua R G, Zhang X, et al. "Regional heterogeneity in expression of the sphingosine-1-phosphate pathway in the female rat lower urinary tract"; Am J Obstet Gynecol 2009; 200:576-7; Chua R G, Calenda G, Zhang X, et al. "Testosterone regulates erectile function and Vcsa1 expression in the corpora of rats"; Mol Cell Endocrinol 2009; 303:67-73. Bladder strips were mounted longitudinally and aortic rings horizontally in a 5 ml organ bath—Multi-Myograph Model 810MS (bladder) or Model 610M (aorta) (Danish Myo Technology; Aarhus, Denmark). The myograph was connected in line to a PowerLab 4/30 Data Acquisition System (ADInstruments; Colorado Springs, Colo.) and in turn to a Dual-Core processor Pentium computer for real-time monitoring of physiological force. The smooth muscle strips were equilibrated at least 1 hour in Krebs-Henseleit (Krebs) buffer at 37° C. with continuous bubbling of 95% O2 and 5% CO2 and buffer was changed every 15 minutes (min). Strips were continuously adjusted to resting tension (0.5 g for rat bladder and 1 g for human bladder (Yamamoto M, Harm S C, Grasser W A, Thiede M A. "Parathyroid hormone-related protein in the rat urinary bladder: a smooth muscle relaxant produced locally in response to mechanical stretch." Proc Natl Acad Sci USA 1992; 89:5326-30. After equilibration, rat detrusor was contracted with 60 mM KCl and the force induced by cumulative concentrations (10-5-10-1 M) of carbachol (CC) or electrical field stimulation (EFS) at varying frequencies of 2-32 Hz, pulse duration 1.5 ms, train 5 s, and 80 V, was normalized to that KCl response. Next, all strips were pre-contracted with 60 mM KCl, or 1 µM CC (rat bladder), or 20 nM endothelin-1 (ET-1) (human bladder) and allowed to reach stable tension and then the relaxant effects of increasing doses of blebbistatin were evaluated. For rat detrusor, after pre-incubation with blebbistatin (10 µM) for 30 min, its inhibitory effect on CC (1 µM) induced contractility or aforementioned EFS mediated contractility was also tested. Additionally, the influence of blebbistatin (10 µM) on rat detrusor spontaneous activity and basal tone was evaluated.

EXAMPLE 2

In Vivo Urodynamic Studies in Rats

Cystometric evaluation of bladder function was performed as previously described on a separate set of 5 rats. See Malmgren A, Andersson P O, Uvelius B. "Bladder function in rats with short- and long-term diabetes; effects of age and muscarinic blockade" J Urol 1989; 142:1608-14; Melman A, Zotova E, Kim M, et al. "Longitudinal studies of time-dependent changes in both bladder and erectile function after streptozotocin-induced diabetes in Fischer 344 male rats" BJU Int 2009, 104:1292-300; Suadicani S O, Urban-Maldonado M, Tar M T, Melman A, Spray D C. "Effects of ageing and streptozotocin-induced diabetes on connexin43 and P2 purinoceptor expression in the rat corpora cavernosa and urinary bladder" BJU Int 2009; 103: 1686-93. Under anesthesia, a PE 50 catheter with a cuff was surgically inserted into the bladder dome and exited through an orifice made in the back of the animal. Cystometrical analyses were performed two days after the surgery, as we showed this to be an optimal period for recovery and investigation. The bladder catheter was connected to a 2-way valve that is, in turn connected to a pressure transducer as well as an infusion pump (model PHD 2000, Harvard Instruments; MA, USA). Rat bladder was infused with vehicle for 30 min and then cystometry was performed. After that, the same rat was treated with 250 nmols blebbistatin for the same period and cystometry was similarly repeated. One rat had bladder over-activity possibly due to post-surgical infection and thus blebbistatin was kept in the bladder for only about 5 min. The rate of infusion of room temperature saline was set at 10 ml/h. Bladder activity was continuously recorded after the first micturition, and subsequently at least 2 h of data were recorded from each rat. Statistical analysis: Results are expressed as mean±SEM for n experiments. Statistical analysis was performed using either the Student's t-test (when two sample treatments were being compared) or using ANOVA when multiple means were compared. p<0.05 was considered significant.

Results: In rat bladder smooth muscle strips in vitro mounted in a tissue bath, both KCl and carbacol (CC) produced phasic-type tension increases. CC dose-response curves were normalized to KCl elicited force and averaged. About 50% of maximum contraction (around 125% of KCl response) was reached at 1 µm and this submaximal contraction was chosen for later experiments.

Figure 2:
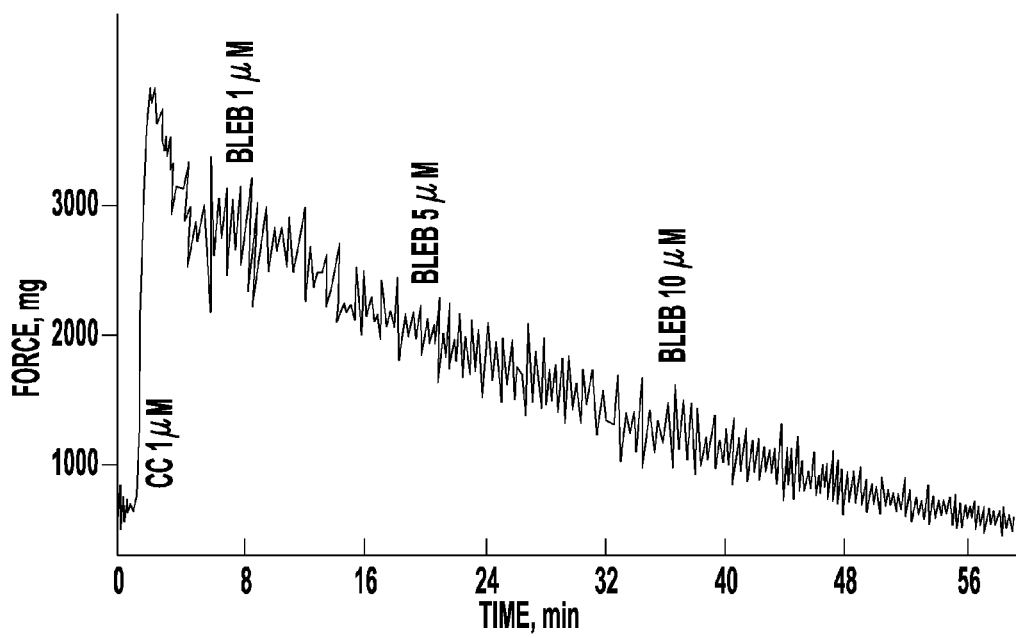
FIG. 2 shows a tracing of the change in tension (contraction) versus time of a rat bladder smooth muscle strip mounted in a tissue bath pre-contracted with 1 uM carbacol (CC) and then relaxed using 1 uM, then 5 uM and then 10 uM BLEB (racemic blebbistatin). The x-axis represents time in minutes (min) while the y-axis represents force (mg). Maximal response to pre-contraction stimulus was taken as 100%, while the relaxant effect of cumulative concentrations (1-10 µM) of BLEB was evaluated as a percentage of this response.

FIG. 1, FIG. 2, and FIG. 3. tracings of bladder strip tension versus time are representative force tracings and rat detrusor (the "as a whole, the bladder muscle") when pre-contracted with 60 mM KCl or 1 µm agonist (CC) can be dose-dependently and completely relaxed by BLEB. On average, blebbistatin relaxed both KCl (FIG. 1) and CC (FIG. 2, FIG. 3) evoked detrusor contraction by 20-30% at 1 µm, 80-100% at 5 µm and more than 100% at 10 µm.

When the rat detrusor muscle (smooth muscle bladder strip) was pre-incubated with 10 µm blebbistatin for 30 min, it not only strongly blunted both CC (FIG. 4A and FIG. 4B) and EFS (FIG. 5A and FIG. 5B) induced detrusor contraction amplitude, it also significantly lowered the basal tone by around 300 mg. In fact, it attenuated CC responsiveness by about 65% (FIG. 4A and FIG. 4B), while blocking EFS-induced stimulation at all frequencies (FIG. 5A and FIG. 5B), but was more pronounced at higher frequencies reaching 50% inhibition at 32 Hz.

Figure 6A:
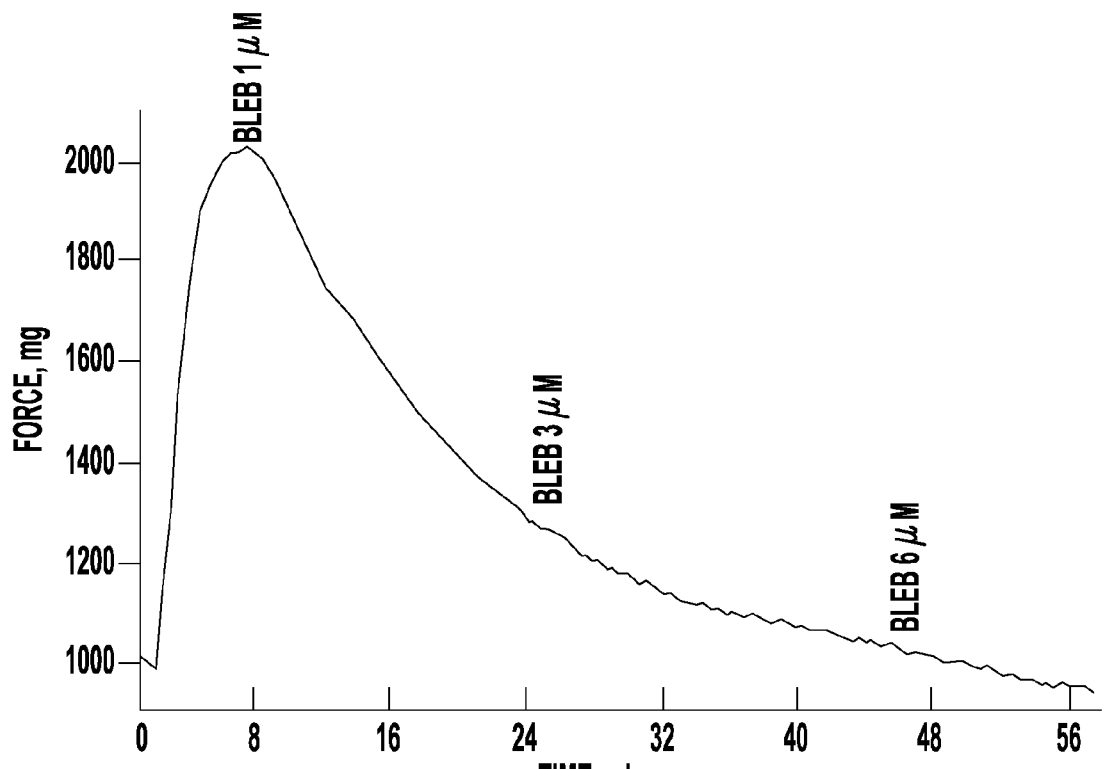
FIG. 6A shows a representative force tracing versus time of BLEB's (racemic blebbistatin's) in vitro relaxant effect on endothelin-1 pre-contracted Human bladder. Human bladder (base bladder near bladder neck) strips were mounted in a tissue bath, pre-contracted with 20 nM endothelin-1 (ET-1) and then treated with cumulative doses of BLEB. The x-axis represents time in minutes (min) while the y-axis represents force (mg).
Figure 6B:
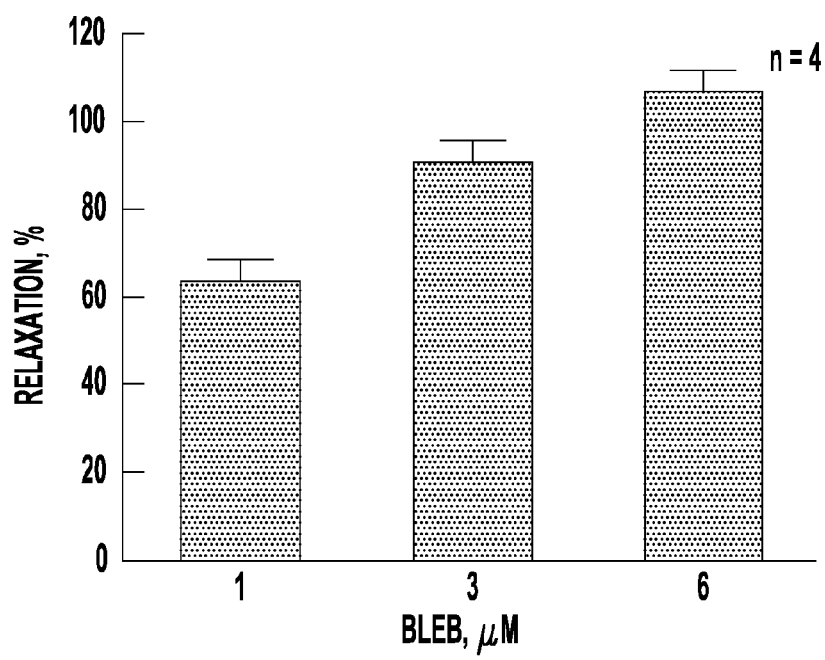
FIG. 6B is a summary graph for the data of FIG. 6A. The maximal response to endothelin-1 (ET-1) was taken as 100%, while the relaxant effect of BLEB (racemic blebbistatin) was evaluated as a percentage of this response. Values are expressed as mean±SEM. (n=4 different strips).

The potent inhibitory profile of blebbistatin was further confirmed in human detrusor smooth muscle obtained from a BPH/LUTS patient bladder base near the bladder neck, as illustrated in FIG. 6A and FIG. 6B. A 1 micromolar (µM), blebbistatin produced 60% relaxation of human bladder that is being pre-contracted with endothelin-1 (ET-1), one of the strongest vasoconstrictors known (20 nM ET-1) and nearly 100% relaxation at 3 µm.

Animal detrusor smooth muscle strips develop spontaneous activity As shown in FIG. 7A and FIG. 7B and Table 1, blebbistatin (10 µm) causes about a 60% decrease ion the amplitude of spontaneous smooth muscle contractions in rat bladder muscle strips (from 287.08±33.23 milligrams (mg) to 118±19.33 mg.) as well as a significant relaxation to the tonus (baseline tension). See FIGS. 4A and 5A. (FIGS. 3A & C).

TABLE 1

Effect of blebbistatin on spontaneous contractions of rat bladder strips

| Treatment | Basal Tone (mg) | Amplitude (mg) | Frequency (cycles/min) |
|---|---|---|---|
| Without blebbistatin | 590 +/− 23 ** | 290 +/− 33 | 4.6 +/− 1.1 |
| With blebbistatin | 310 +/− 16 | 120 +/− 19 | 5.5 +/− 1.2 | n = 15 strips from 6 different rats,
** <0.01 vs with blebbistatin.

EXAMPLE 3

Figure 8A:
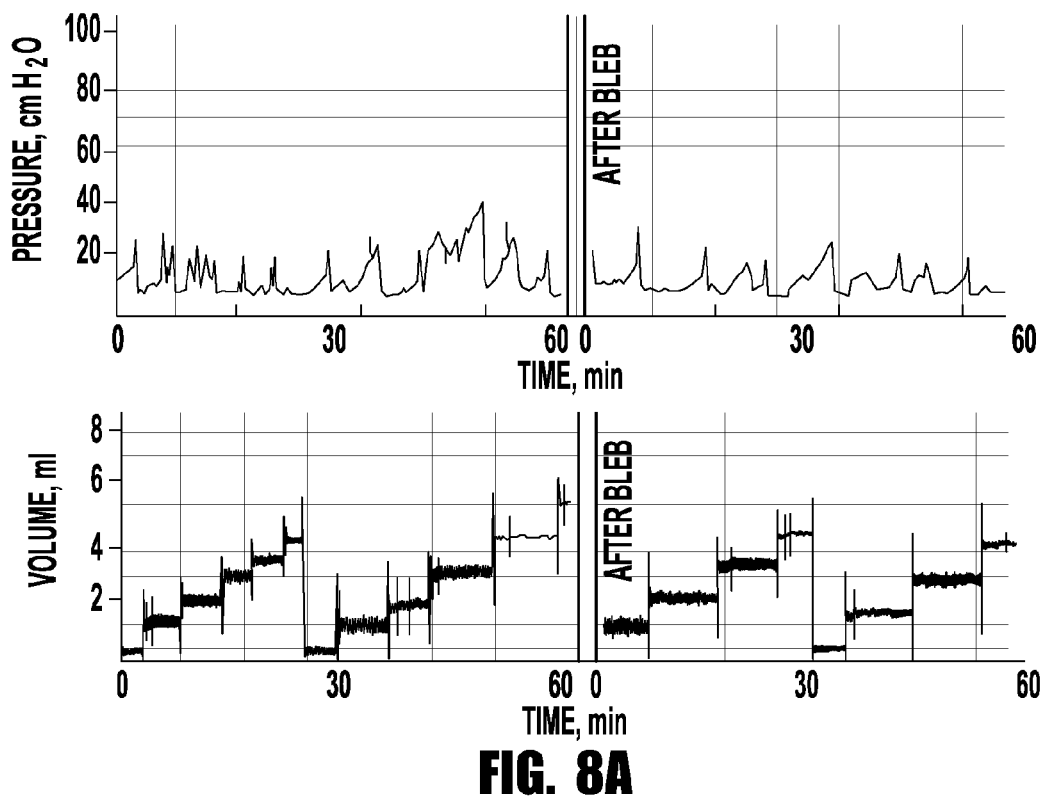
FIG. 8A shows urodynamics of a bladder in an awake rat. After 90 minutes of saline infusion into bladder, there is an infusion of 250 nanomolar BLEB (racemic blebbistatin). Upper panels depict intravesical pressure (x-axis=minutes time and y-axis=pressure in cm $H_2O$. Lower panels give volume and frequency of micturation (urine voiding of bladder). The x-axis represents time in minutes (min) while the y-axis represents volume (ml). Left side panels are control experiments with saline vehicle infusion while right side panels are after infusion of BLEB.

Experimental In vivo instillation of 250 nanomolar blebbistatin into the normal awake Rat Bladder FIG. 8A shows typical rat cystometric tracings in which the bladder has been pre-treated with vehicle (left panels) or blebbistatin (right panels) for 30 min. The urodynamic parameters are summarized in Table 2 below. Table 2 shows that BLEB significantly increased bladder capacity, micturition volume and compliance while micturition frequency was obviously decreased. Intravesical pressure was not significantly influenced by blebbistatin. FIG. B is the uroflow tracing of the rat with overactive bladder treated with vehicle (upper panel) or blebbistatin (lower panel). Consistent with human BPH/LUTS bladder strips (obtained from simple human prostatectomy operations) in vitro observations, rats with OAB are more sensitive to blebbistatin with voiding frequency declining by over 50%.

TABLE 2

Impact of blebbistatin on UroDynamic Parameters of Awake Rats (n = 5)

| Treatment | BC (ml) | MV (ml) | RV (ml) |
|---|---|---|---|
| Vehicle | 0.78 +/− 0.15 | 0.76 +/− 0.15 | 0.02 +/− 0.01 |
| Blebbistatin | 1.4 +/− 0.16 * | 1.4 +/− 10 * | 0.03 +/− 0.01 |

| Treatment | BP (cm H20) | MP (cmH20) | Bcom (ml) | MF (ml) |
|---|---|---|---|---|
| Vehicle | 7.1 +\− 0.91 | 40 +/− 12 | 0.16 +/− 0.01 | 13 +/− 3.3 |
| Blebbistatin | 6.9 +/− 1.8 | 42 +/− 13 | 0.28 +/− 0.02 | 7.2 +/− 1.3 * |

Bladder function was evaluated using the following urodynamic criteria: bladder capacity: (BC =volume of infused saline discharged at micturition); micturition volume (MV =the volume of urine discharged during micturation); micturition); residual volume (RV =volume of infused saline minus micturition volume); basal pressure (BP =the lowest average bladder pressure recorded during cystometry); micturition] pressure (MP =peak bladder pressure during); micturition); Bcom =bladder compliance; MF =micturition frequency; * <0.05 vs vehicle.

Studies reported regarding the present invention indicate that in vitro in a tissue bath, the smooth muscle rat bladder strips generated fast phasic-type contraction elicited by potassium chloride (KCl) depolarization or carbacol (CC) evoked activation of the muscarinic system (FIG. 1, FIG. 2 and FIG. 3). Neither method of inducing a phasic contraction in the smooth muscle bladder strip influenced the means by which the smooth muscle bladder strip relaxed.

Figure 4A:
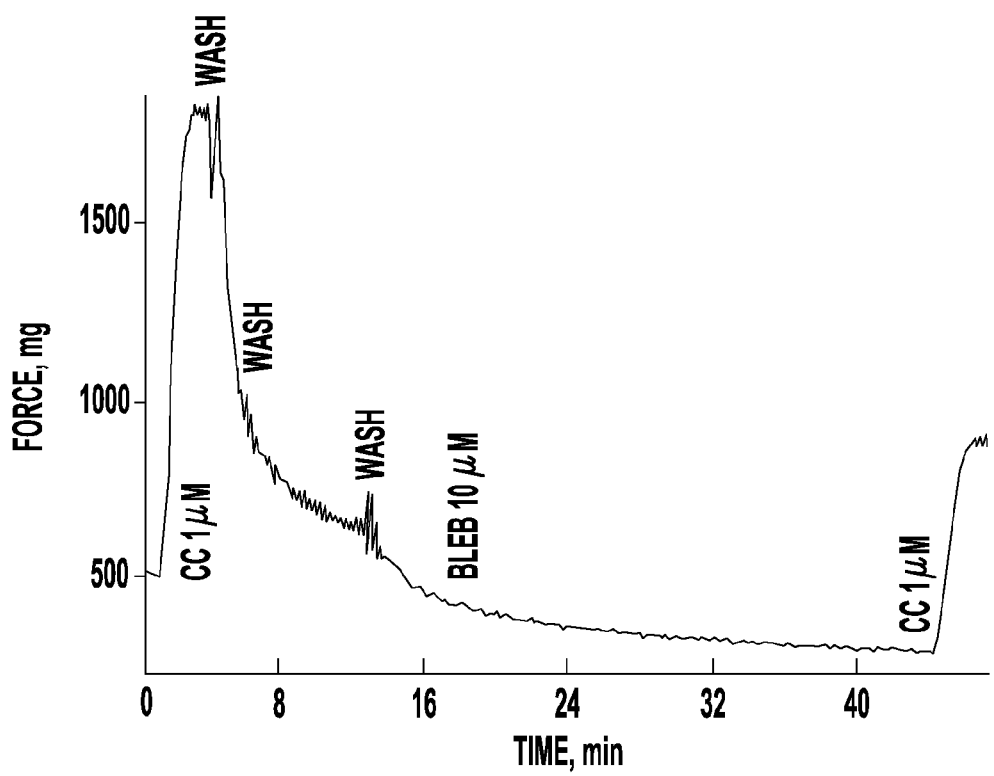
FIG. 4A shows a tracing of the change in tension (contraction) versus time of a rat bladder smooth muscle strip mounted in a tissue bath pre-contracted with 1 uM carbacol (CC). After several washes without drug to return tension to the basal state, then the detrusor muscle (bladder smooth muscle) was pre-incubated with 10 µM BLEB (racemic blebbistatin) for 30 minutes (min). The tissue was pre-contracted again with 1 uM carbacol while in the presence of 10 uM BLEB.
Figure 4B:
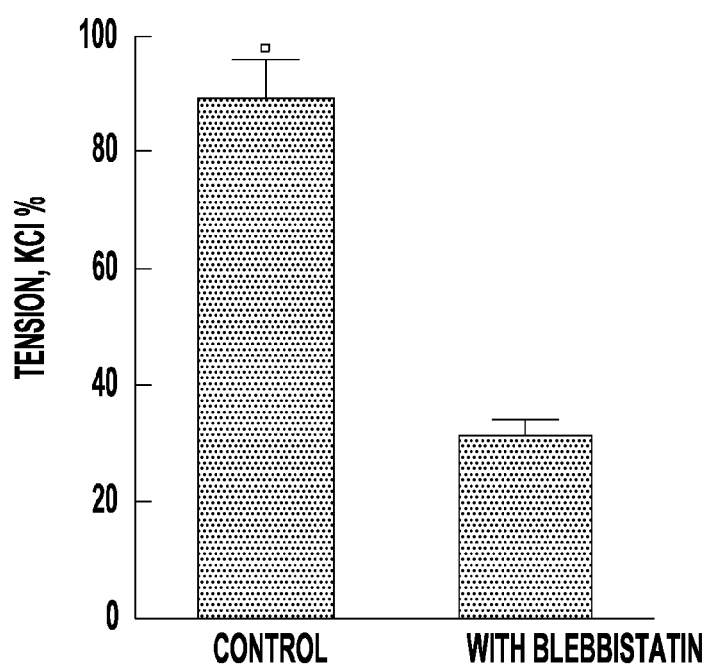
FIG. 4B shows a summary graph for the data of FIG. 4A. **=p<0.01 vs with BLEB (racemic blebbistatin). (n=4 strips obtained from 4 different animals).
Figure 5B:
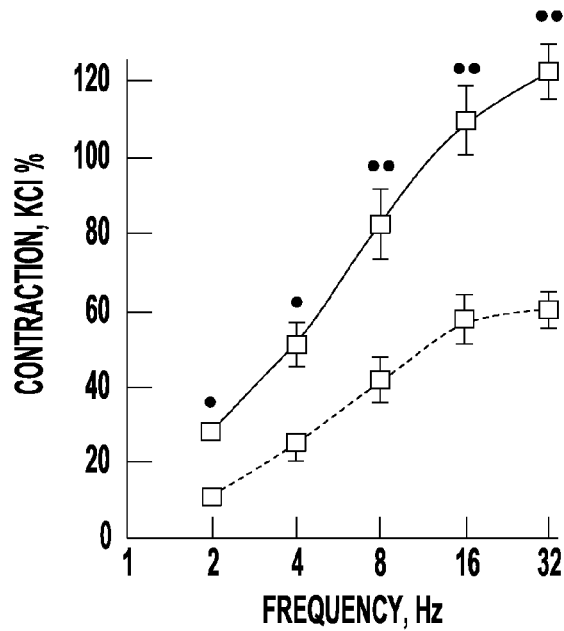
FIG. 5B is a summary graph for the contraction data of FIG. 5A at EFS frequencies 2 Hz, 4 Hz, 8 Hz and 16 Hz with or without 10 µM BLEB (racemic blebbistatin) as a percentage of maximal contraction induced by 60 mM KCl. (*=p<0.05 vs with BLEB); (**=p<0.01 vs with BLEB). (n=4 strips obtained from 4 different animals).

In vitro relaxation in response to blebbistatin was dose-dependent: with basal tension decreasing by 20-30% at 1 μm, 80-100% at 5 μm and over 100% at 10 lam. In vitro pre-incubation of bladder strips with BLEB (10 μM) for 30 minutes attenuated a carbacol-mediated bladder strip contraction by about 65% while EFS-evoked contraction was attenuated frequency by frequency reaching at 32 Hz by about 50%. Peak contraction force and steady-state tension were strongly reduced (FIG. 4A and FIG. 4B). The time needed for blebbistatin to relax the muscle strip in vitro in a tissue bath was 30-60 minutes whereas muscarinic receptor antagonists such as atropine inhibit relaxation in 3-5 minutes.

In vitro experiments related to the present invention, rat smooth muscle bladder strips exhibited spontaneous contractions which 10 uM BLEB significantly reduced in spontaneous contraction amplitude and in basal tone (FIG. 7A and FIG. 7B and Table 2. Thus, the present experiments are support the utility of the present invention as therapeutic means for treating OAB.

Human bladder base smooth muscle tissue from open prostatectomy operations was studied to test the utility of the present invention. BLEB induced a strong, dose-dependent relaxation of human bladder in vitro tissue (FIG. 6A and FIG. 6B). In vitro, blebbistatin at a dose of 1 μM caused a 60% relaxation of human bladder tissue that had been pre-contracted with Endothelin-1 (ET-1) a strong vasoconstrictor. A BPH/LUTS bladder may have an enhanced response to blebbistatin due to distension or inflammation of the overactive bladder (Lavelle J P, Meyers S A, Ruiz W G, Buffington C A, Zeidel M L, Apodaca G. "Urothelial pathophysiological changes in feline interstitial cystitis: a human model" Am J Physiol Renal Physiol 2000; 278: F540-F553).

Figure 8B:
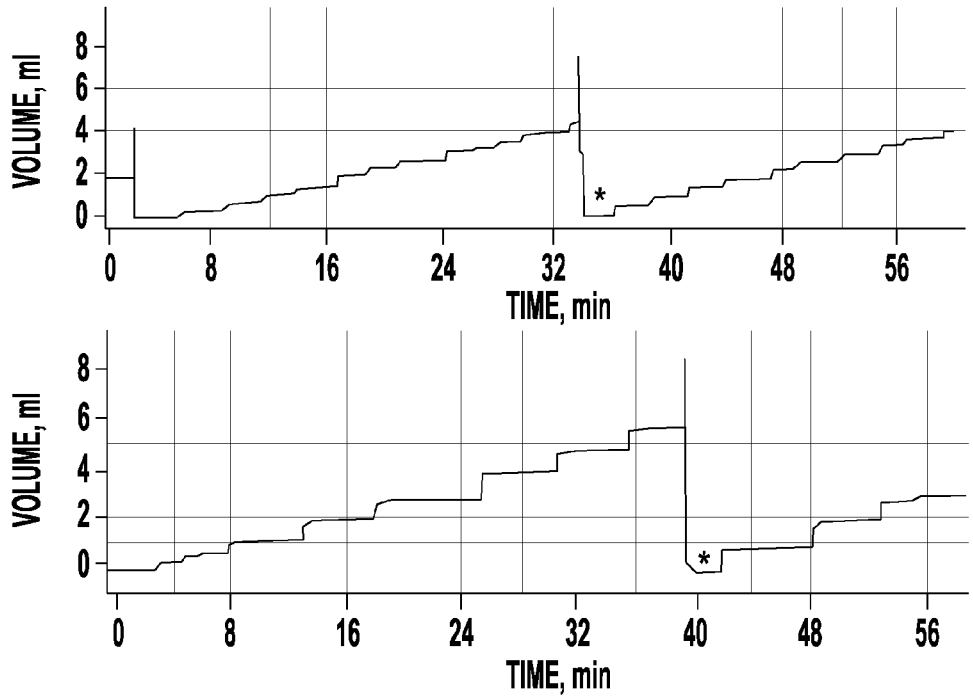
FIG. 8B shows urodynamics of an overactive bladder in an awake rat. The * represents when urine collection tube had to be emptied as it was full. Upper panel is a control experiment with saline while lower panel is urodynamics of the bladder after an infusion of 250 nanomolar BLEB (racemic blebbistatin). Volume and frequency of micturation by the rat with the overactive bladder decrease due to BLEB. The x-axis represents time (min) while the y-axis represents volume (ml).

In one experiment testing the utility of the present invention, 250 nanomolar BLEB was instilled into the bladder of a normal awake rat. The intra-bladder administration of blebbistatin effectively inhibited contractility, increased bladder capacity, volume of micturition and bladder compliance while decreasing the frequency of urination (FIG. 8A, FIG. 8B and Table. 2). In vivo, in an experiment with a rat suffering OAB, BLEB was more effective than in the rat with a normal functioning bladder.

EQUIVALENTS

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls. The section headings used herein are for organizational purposes only and are not to be construed as limiting the subject matter described in any way.

While the present inventions have been described in conjunction with various embodiments and examples, it is not intended that the present teachings be limited to such embodiments or examples. On the contrary, the present inventions encompass various alternatives, modifications, and equivalents, as will be appreciated by those of skill in the art. The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

The invention claimed is:

1. A method of treating an overactive bladder in a patient, which method comprises:
    administering to the patient an effective amount of a Myosin II ATPase inhibitor selected from the group consisting of a Formula (I) compound, a salt of the Formula (I) compound, a racemic mixture of the Formula (I) compound, an enantiomer of the Formula (I) compound, and any combination thereof, to treat the overactive bladder in the patient,

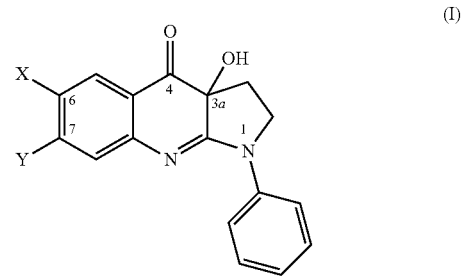

(I)

including:
    selecting an X substituent from the group consisting of hydrogen; and
    selecting a Y substituent from the group consisting of $(C_{1-6})$alkyl, thio, $(C_{1-6})$alkylthio, thio$(C_{1-6})$alkyl, halo$(C_{1-6})$alkyl, $(C_{2-6})$alkenyl, $(C_{1-6})$alkylamino, amino$(C_{1-6})$alkyl, hydroxy, $(C_{1-6})$alkoxy, hydroxy$(C_{1-6})$alkyl, carboxy, phenyl, $(C_{1-6})$alkylphenyl, phenyl$(C_{1-6})$alkyl, furanyl, pyridyl, piperazinyl, cycloheptyl, cyclohexyl, cyclopentyl, cyclobutyl, cyclobutenyl, cycloheptenyl, cyclohexenyl, fluoro, chloro, bromo, iodo, cyclopentenyl, nitro, anilino, anilino$(C_{1-6})$alkyl, pyrazinyl, $(C_{1-6})$alkynl, aminocyclohexyl, aminocyclopropyl, aminocyclobutyl, aminocyclopentyl, and aminocycloheptyl.

2. The method according to claim 1,
    selecting the X substituent from the group consisting of hydrogen; and
    selecting the Y substituent from the group consisting of $(C_{1-6})$alkyl, halo$(C_{1-6})$alkyl, amino$(C_{1-6})$alkyl, hydroxy, $(C_{1-6})$alkoxy, hydroxy$(C_{1-6})$alkyl, carboxy, phenyl, $(C_{1-6})$alkylphenyl, phenyl$(C_{1-6})$alkyl, furanyl, pyridyl, piperazinyl, cycloheptyl, cyclohexyl, cyclopentyl, cyclobutyl, cyclobutenyl, fluoro, chloro, bromo, iodo, cyclopentenyl, nitro, anilino, anilino$(C_{1-6})$alkyl, pyrazinyl, and $(C_{1-6})$alkynyl, $(C_{1-6})$alkyl$(C_{3-7})$cycloalkyl, and $(C_{3-7})$cycloalkyl$(C_{1-6})$alkyl.

3. The method, according to claim 1,
selecting the X substituent from the group consisting of hydrogen; and
selecting the Y substituent from the group consisting of $(C_{1-6})$alkyl, halo$(C_{1-6})$alkyl, $(C_{1-6})$alkoxy, phenyl, phenyl$(C_{1-6})$alkyl, furanyl, pyridyl, piperazinyl, fluoro, chloro, bromo, iodo, cyclopentenyl, and nitro $(C_{1-6})$alkyl$(C_{3-7})$cycloalkyl, and $(C_{3-7})$cycloalkyl$(C_{1-6})$alkyl.

4. The method according to claim 1,
selecting the X substituent from the group consisting of hydrogen; and
selecting the Y substituent from the group consisting of furanyl, pyridyl, piperazinyl, fluoro, chloro, bromo, iodo, cyclopentenyl, nitro, anilino, aniline$(C_{1-6})$alkyl, and pyrazinyl.

5. The method according to claim 1,
selecting the X substituent from the group consisting of hydrogen; and
selecting the Y substituent from the group consisting of $(C_{1-6})$alkyl, fluoro, chloro, bromo, furanyl, pyridyl, piperazinyl, aminocyclopropyl, aminocyclobutyl, and aminocyclopentyl.

6. The method according to claim 1,
selecting the X substituent from the group consisting of hydrogen; and
selecting the Y substituent from the group consisting of phenyl, phenyl$(C_{1-6})$alkyl, furanyl, pyridyl, fluoro, chloro, bromo, iodo, pyrazinyl, and $(C_{1-6})$alkynyl, and $(C_{4-6})$cycloalkyl$(C_{1-6})$alkyl.

7. The method according to claim 1,
selecting the X substituent from the group consisting of hydrogen, and 2-fluoroethyl; and
selecting the Y substituent from the group consisting of nitro.

8. The method according to claim 1,
selecting the X substituent from the group consisting of hydrogen; and
selecting the Y substituent from the group consisting of bromo, and iodo.

9. The method according to claim 1,
selecting the X substituent from the group consisting of hydrogen; and
selecting the Y substituent from the group consisting of bromo.

10. The method according to claim 1,
selecting the X substituent from the group consisting of hydrogen; and
selecting the Y substituent from the group consisting of furanyl, pyridyl, and pyrazinyl.

11. The method according to claim 1, further including;
selecting the salt of the Formula (I) compound from the group consisting of hydrochloride, sulfate, acetate, phosphate, maleate, citrate, nitrate, tosylate, and mesylate.

12. The method according to claim 1, further including:
delivering the effective amount of the Myosin II ATPase inhibitor to the bladder in the patient by a route of administration selected from the group consisting of an oral route, an intravenous injection route, a subcutaneous injection route, an intramuscular injection route, a nasal route; a transdermal route, a direct injection route into a bladder intra-vesicular space, the direct injection route by a cannula into the bladder intra-vesicular space, the direct injection route by the cannula into the bladder intra-vesicular space with the cannula connected to a drug reservoir-pumping device located outside the bladder, the direct delivery route by the drug reservoir-pumping device located in the bladder intra-vesicular space, the direct delivery route by a cannula in a ureter, the direct delivery route by the cannula in a urethra, and a combination of the routes thereof.

* * * * *